US006331663B1

(12) United States Patent
Kloti

(10) Patent No.: US 6,331,663 B1
(45) Date of Patent: Dec. 18, 2001

(54) MODIFIED FULL LENGTH PROMOTERS

(75) Inventor: Andreas S. Kloti, Durham, NC (US)

(73) Assignee: Paradigm Genetics, Inc., Research Triangle Park, NC (US)

( * ) Notice: Subject to any disclaimer, the term of this patent is extended or adjusted under 35 U.S.C. 154(b) by 0 days.

(21) Appl. No.: 09/459,427

(22) Filed: Dec. 13, 1999

(51) Int. Cl.[7] ............................... A01H 5/00; A01H 5/10; C12N 5/04; C12N 15/82

(52) U.S. Cl. ....................... 800/278; 435/320.1; 435/419; 435/468; 536/24.1; 800/298; 800/306; 800/320.02

(58) Field of Search ................................ 435/320.1, 419, 435/468; 536/24.1; 800/287, 298, 278, 306, 320.2

(56) References Cited

U.S. PATENT DOCUMENTS

| | | |
|---|---|---|
| 5,097,025 | 3/1992 | Benfey et al. . |
| 5,312,910 | 5/1994 | Ganesh et al. . |

FOREIGN PATENT DOCUMENTS

| | | |
|---|---|---|
| 0426641 | 10/1990 | (EP) . |
| 9800534 | 1/1998 | (WO) . |
| 9927119 | 6/1999 | (WO) . |
| 9943938 | 9/1999 | (WO) . |

OTHER PUBLICATIONS

P. Benefey et al, "The Caulflower Mosaic Virus 35S Promoter: Combinatorial Regulatioin of Transcription in Plants", Nov. 1990, Science vol. 250, pp. 959–966.*

Y. Kim et al, "a 20 nucleotide upstream element is essential for the nopaline synthase (nos) promoter activity", 1994, Plant Molecular Biology vol. 24, pp 105–117.*

* cited by examiner

*Primary Examiner*—David T. Fox
*Assistant Examiner*—Cynthia Collins
(74) *Attorney, Agent, or Firm*—Joseph T. Majka; Henry P. Nowak

(57) ABSTRACT

This invention relates to plants, seeds and DNA constructs containing DNA that is either SEQ ID NO:10, SEQ ID NO:11, or SEQ ID NO:20, or the complementary or double stranded sequence thereof, as well as a method for their preparation.

20 Claims, 15 Drawing Sheets

MODIFIED FULL LENGTH PROMOTERS

FIELD OF THE INVENTION

The present invention relates to highly effective modified full-length promoters for plants, such as soybeans and rice.

BACKGROUND OF THE INVENTION

Recent advances in genetic engineering have provided plant breeders and geneticists with the tools to insert or transform genes, which are selected portions of deoxyribonucleic acid (also known as DNA), into a plant in order to produce new kinds of plants known as transgenic plants. Such transgenic plants or crops can have unique characteristics or traits, including resistance to plant diseases, resistance to herbicides, resistance to insects, enhanced stability or shelf-life of the ultimate consumer product obtained from the plant and/or improvements in the nutritional value in the edible portions of the plant. Genes are made up of DNA, a complex molecule inside each plant cell that provides the instructions for all aspects of the plant's growth. A promoter is a region on a gene where transcription factors can bind to enable the gene to "express" itself through the production of another, but smaller molecule known as messenger RNA. Messenger RNA enables the gene to "deliver" its message or instructions to other parts of the plant cell in many cases by being translated into a protein. Various plant promoters have been identified and isolated from different plants, as described in various patents, such as U.S. Pat. Nos. 5,536,653; 5,589,583; 5,608,150; and 5,898,096. Although effective, such promoters have not been modified or optimized to provide enhanced or improved characteristics or traits. It would be desirable to provide plant promoters that have been modified to advantageously provide improved characteristics or traits in plants.

SUMMARY OF THE INVENTION

The present invention relates to a modified promoter that when placed upstream of a gene of interest, will cause that gene to be expressed in plant tissues. The promoter should be active during most of the plant's developmental stages from the seedling stage to maturity.

In a first embodiment, the present invention is directed to a DNA molecule that is SEQ ID NO: 10, wherein nucleotide "w" is "a or t/u" (adenine or thymine/uracil); and nucleotide "y" is "t/u or c"(thymine/uracil or cytosine). Preferably, the DNA molecule is SEQ ID NO: 11 and SEQ ID NO: 20, as follows:

```
aatgaagtcc caatcctagt ggtcactttt gaaaggaacc ttggcaaagg agggtggctt   [SEQ ID NO:10]
gcaagtgcca tccttgcrat aaaggaaagg tgaaggatca aggtgcccct accaamagtg
gtcttgcctt tggtccccca cccaagagga gcatcctagt acaagtgggg aatccaacca
cgtcttcgca agwggrttgw tgtgayatct ccattgaygt aagggatgac gcacaaagtg
actatccttc acaagacctt cctctatata aggaggggtt cattcccatt tgaaggatca
ata

aatgaagtcc caatcctagt ggtcactttt gaaaggaacc ttggcaaagg agggtggctt   [SEQ ID NO:11]
gcaagtgcca tccttgcgat aaaggaaagg tgaaggatca aggtgcccct accaacagtg
gtcttgcctt tggtccccca cccaagagga gcatcctagt acaagtgggg aatccaacca
cgtcttcgca agagggttgt tgtgacatct ccattgatgt aagggatgac gcacaaagtg
actatccttc acaagacctt cctctatata aggaggggtt cattcccatt tgaaggatca
ata

aatgaagtcc caatcctagt ggtcactttt gaaaggaacc ttggcaaagg agggtggctt   [SEQ ID NO:20]
gcaagtgcca tccttgcaat aaaggaaagg tgaaggatca aggtgcccct accaaaagtg
gtcttgcctt tggtccccca cccaagagga gcatcctagt acaagtgggg aatccaacca
cgtcttcgca agtggattga tgtgatatct ccattgacgt aagggatgac gcacaaagtg
actatccttc acaagacctt cctctatata aggaggggtt cattcccatt tgaaggatca
ata
```

In its double stranded form, SEQ ID NOS: 10, 11 and 20 are useful as full length promoters in plants, such as dicots and monocots.

In a second embodiment, the present invention is directed toward a DNA construct comprising a DNA molecule that contains SEQ ID NO: 10, SEQ ID NO: 11 or SEQ ID NO: 20. Preferably the DNA construct is a plasmid. Also preferred is that the plasmid is of the designation pPG345 or pPG346.

In a third embodiment, the present invention is directed toward a eukaryotic cell comprising a DNA molecule that contains SEQ ID NO: 10, SEQ ID NO: 11 or SEQ ID NO: 20. Preferably, the eukaryotic cell is a plant cell. Also preferred is that the eukaryotic plant cell is a dicot plant cell. However, the eukaryotic plant cell may also be a monocot plant cell.

In a fourth embodiment, the present invention is directed toward a plant having eukaryotic cells comprising a DNA molecule that contains SEQ ID NO: 10, SEQ ID NO: 11 or SEQ ID NO: 20. Preferably, the plant is a dicot plant, although the plant may also be a monocot plant. Also preferred is that the dicot plant is *Arabidopsis thaliana.*

In a fifth embodiment, the present invention is directed toward seed capable of producing a plant having cells comprising a DNA molecule that contains SEQ ID NO: 10, SEQ ID NO: 11 or SEQ ID NO: 20. Preferably, the seed is capable of producing a plant that is a dicot plant, although the seed may also be able to produce a plant that is a monocot plant.

In a sixth embodiment, the present invention is directed toward a method of controlling and/or increasing the transcription of a heterologous or homologous gene in a plant or plant tissue comprising transforming the plant or plant tissue with a DNA construct comprising a heterologous or homologous gene and a DNA molecule that is SEQ ID NO: 10, SEQ ID NO: 11 or SEQ ID NO: 20.

One advantage of the present invention is that it provides a promoter that can better resist cytosin methylation (at CG or CNG di- or tri-nucleotides) which can deactivate or reduce the effectiveness of the promoter, compared to other known promoters, such as from double-stranded DNA viruses.

DETAILED DESCRIPTION OF THE INVENTION

Figure 1:
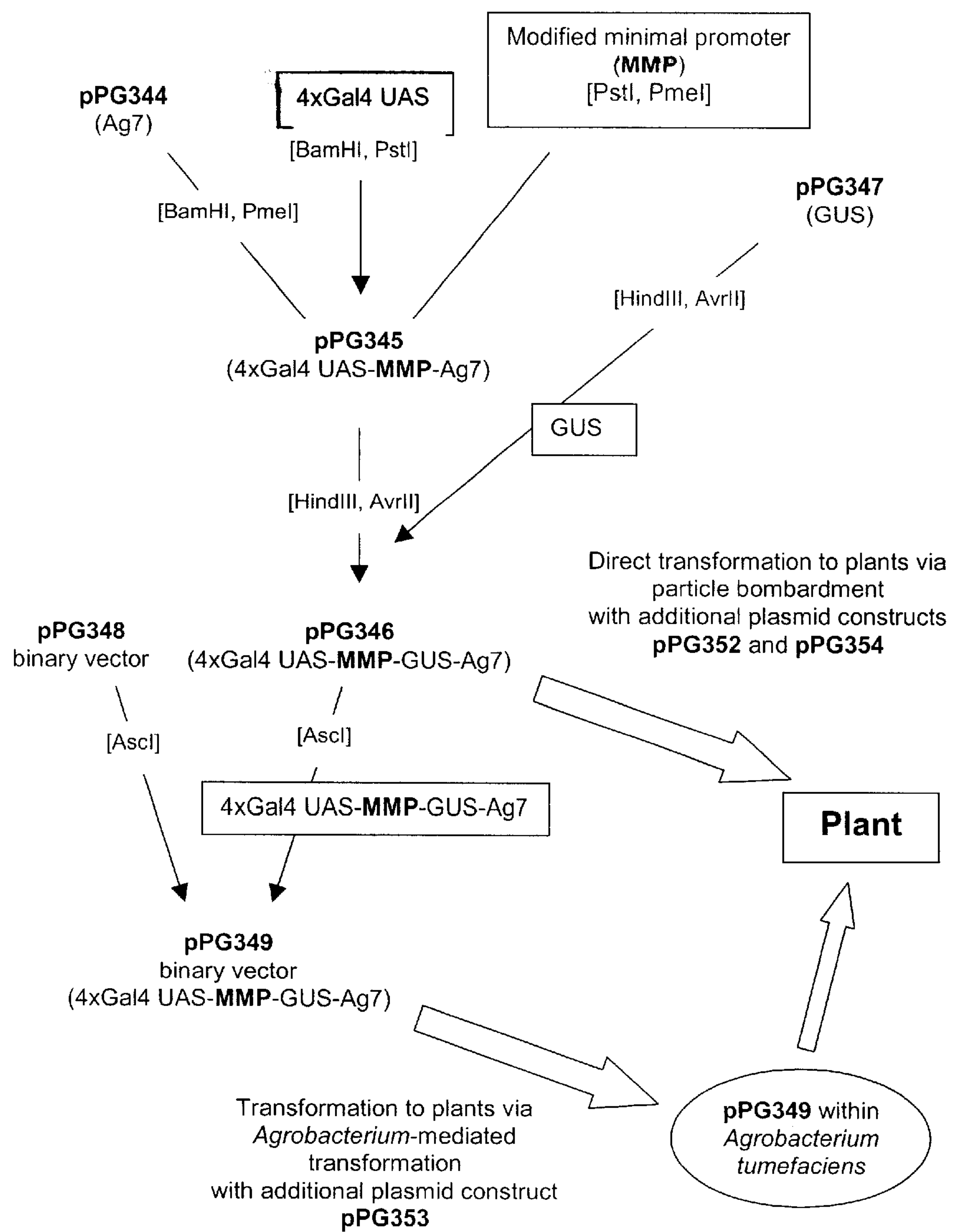
FIG. 1 is a diagram of the procedure for cloning of the minimal promoter into a suitable DNA construct.

The present invention will now be described more fully hereinafter with reference to the accompanying figures or drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs.

"Promoter" refers to the nucleotide sequences at the upstream or 5' end of a structural gene which direct the initiation of transcription. Generally, promoter sequences are necessary to drive the expression of a downstream gene. The promoter binds RNA polymerase and accessory proteins, forming a complex that initiates transcription of the downstream nucleotide sequence. In the construction of heterologous promoter/structural gene combinations, the structural gene is placed under the regulatory control of a promoter such that the expression of the gene is controlled by promoter sequences. The promoter is positioned preferentially upstream of the structural gene, i.e., the amino acid coding region, and at a distance that approximates the distance between the promoter and the protein encoding region in its natural setting. As is known in the art, some variation in this distance can be tolerated without loss of promoter function.

As used herein, the term "operatively linked" means that a promoter is connected to a coding region in such a way that the transcription of that coding region is controlled and regulated by that promoter.

The term "nucleic acid sequence" as used herein refers to a nucleotide, oligonucleotide, or polynucleotide, and fragments thereof, and to DNA or RNA of genomic or synthetic origin which may be single- or double-stranded, and which may represent a sense or antisense strand.

"Chemically synthesized," as related to a sequence of DNA, means that the component nucleotides are assembled in vitro. Manual chemical synthesis of DNA may be accomplished using well established techniques as known in the art. For example, automated chemical synthesis of DNA can be performed using one of a number of commercially available apparatus.

"Gene" refers to a unit composed of a promoter region, a structural gene region and a transcription termination region.

"Expression" refers to the transcription and in the case of a protein gene product, translation, of a heterologous or homologous gene to yield the gene product encoded by the structural portion of the gene.

"Gene product" refers to a specific protein or RNA product derived from the structural portion of the gene.

"Heterologous" is used to indicate that a nucleic acid sequence (e.g., a gene) or a protein has a different natural origin or source with respect to its current host. Heterologous is also used to indicate that one or more of the domains present in a protein differ in their natural origin with respect to other domains present. In cases where a portion of a heterologous gene originates from a different organism the heterologous gene is also known as a chimera.

"Homologous" is used to indicate that a nucleic acid sequence (e.g. a gene) or a protein has a similar or the same natural origin or source with respect to its current host.

"Structural gene" is that portion of a gene comprising a DNA segment encoding the gene product, RNA or protein, and excluding the 5' sequence which drives the initiation of transcription. The structural gene may be one which is normally found in the cell or one which is not normally found in the cell wherein it is introduced, in which case it is termed a heterologous gene. A heterologous or homologous gene may be derived in whole or in part from any source known to the art, including a bacterial genome or episome, eukaryotic, nuclear or episomal DNA, organellar DNA e.g., mitochondrial or chloroplast DNA, cDNA, viral DNA or chemically synthesized DNA. A structural gene may contain one or more modifications in the coding region which could affect the chemical structure and/or the biological activity of gene product. Such modifications include, but are not limited to, mutations, insertions, deletions and substitutions of one or more nucleotides. The structural gene may constitute an uninterrupted coding sequence or it may include one or more introns, flanked by appropriate splice junctions. The structural gene may be a composite of segments derived from a plurality of sources, either naturally occurring or synthetic, or both.

"Gene product" refers to a specific protein or RNA product derived from the coding sequence.

"Transcription" is the process by which a downstream nucleotide sequence is "read" to produce a messenger RNA (mRNA). When the gene product is a specific protein, the mRNA is the molecule that is "read" by the translational machinery to produce that protein. Variable regions at the beginning, i.e., 5' end, and the end, i.e., 3' end of the gene may or may not code for amino acids. Regions such as these are referred to as 5' untranslated region (5' UTR) and 3' untranslated region (3' UTR) respectively. A portion of the 5' UTR serves as the binding region for the translational machinery (e.g., ribosomes and accessory proteins) required to synthesize a protein gene product encoded by an mRNA.

The promoter of the present invention set forth herein can be efficiently expressed in higher eukaryotes (e.g., plants), and more specifically will be more efficiently expressed in dicotyledenous plants, which include but are by no means limited to species of legumes (from the family Fabaceae), including soybean, peanut, and alfalfa; species of the Solanaceae family such as tomato, eggplant and potato; species of the family Brassicaceae such as cabbage, turnips and rapeseed; species of the family Rosaceae such as apples, pears and berries; and members of the families Cucurbitaceae (cucumbers), Chenopodiaceae (beets) and Umbelliferae (carrots).

The present invention provides an advantageously modified DNA promoter for the enhanced expression of desired heterologous or homologous protein genes in transgenic plants. To this end, one embodiment of the present invention is a DNA construct comprising a DNA sequence encoding the modified promoter. Such DNA constructs accordingly provide for the preparation of stably transformed cells expressing heterologous protein, which transformed cells are also an aspect of the invention. Still further, the modified promoters of the present invention provide for the subsequent regeneration of fertile, transgenic plants and progeny containing desired modified promoters. These aspects of the invention are further described herein below.

DNA constructs (also referred to herein as DNA vectors) of the present invention comprise the nucleotide sequence of the modified promoters, which nucleotide sequence is preferably the sequence provided herein as SEQ ID NO: 10, SEQ ID NO: 11 or SEQ ID NO: 20. The preparation of DNA constructs is known in the art. See, e.g., Sambrook et al., *Molecular Cloning: A Laboratory Manual* (1989). DNA constructs of the present invention contain the modified promoter for the expression of heterologous or homologous genes in plants.

The DNA sequences that comprise the DNA constructs of the present invention are preferably carried on suitable vectors, which are known in the art. Preferred vectors are plasmids that may be propagated in bacteria, such as *E. coli*. Particularly preferred vectors for transformation are those useful for transformation of plant cells by Agrobacteria, as described further below. For Agrobacterium-mediated transformation, the preferred vector is a Ti-plasmid derived vector. Other appropriate vectors which can be utilized as starting materials are known in the art. Suitable vectors for transforming plant tissue and protoplasts have been described by deFramond, A. et al., *Bio/Technology* 1, 263 (1983); An, G. et al., *EMBO J.* 4, 277 (1985); and Rothstein, S. J. et al., *Gene* 53, 153 (1987). In addition to these, many other vectors have been described in the art which are suitable for use as starting materials in the present invention.

The DNA encoding the modified promoter of the present invention, and the DNA constructs comprising them, have applicability to any structural gene that is desired to be introduced into a plant to provide any desired characteristic in the plant, such as herbicide tolerance, virus tolerance, insect tolerance, disease tolerance, drought tolerance, or enhanced or improved phenotypic characteristics such as improved nutritional or processing characteristics.

Transgenes (heterologous or homologous genes to be transformed into a plant cell) will often be genes that direct the expression of a particular protein or polypeptide product, but they may also be non-expressible DNA segments, e.g., transposons that do not direct their own transposition. As used herein, an "expressible gene" is any gene that is capable of being transcribed into RNA (e.g., mRNA, antisense RNA, etc.) or translated into a protein, expressed as a trait of interest, or the like, etc., and is not limited to selectable, screenable or non-selectable marker genes. The invention also contemplates that, where both an expressible gene that is not necessarily a marker gene is employed in combination with a marker gene, one may employ the separate genes on either the same or different DNA segments for transformation. In the latter case, the different vectors are delivered concurrently to recipient cells to maximize cotransformation.

Any heterologous gene or nucleic acid that is desired to be expressed in a plant is suitable for the practice of the present invention. Heterologous genes to be transformed and expressed in the plants of the present invention include but are not limited to genes that encode resistance to diseases and insects, genes conferring nutritional value, genes conferring antifungal, antibacterial or antiviral activity, and the like. Alternatively, therapeutic (e.g., for veterinary or medical uses) or immunogenic (e.g., for vaccination) peptides and proteins can be expressed in plants transformed with the minimal promoters of the present invention. Likewise, the transfer of any nucleic acid for controlling gene expression in a plant is contemplated as an aspect of the present invention. For example, the nucleic acid to be transferred can encode an antisense oligonucleotide. Alternately, plants may be transformed with one or more genes to reproduce enzymatic pathways for chemical synthesis or other industrial processes.

In order to improve the ability to identify transformants, one may desire to employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the GUS gene). Of course, many examples of suitable marker genes are known to the art and can be employed in the practice of the invention. The selectable marker gene may be the only heterologous gene expressed by a transformed cell, or may be expressed in addition to another heterologous gene transformed into and expressed in the transformed cell. Selectable marker genes are utilized for the identification and selection of transformed cells or tissues. Selectable marker genes include genes encoding antibiotic resistance, such as those encoding neomycin phosphotransferase II (NEO) and hygromycin phosphotransferase (HPT), as well as genes conferring resistance to herbicidal compounds. Herbicide resistance genes generally code for a modified target protein insensitive to the herbicide or for an enzyme that degrades or detoxifies the herbicide in the plant before it can act. See, DeBlock et al., *EMBO J.* 6, 2513 (1987); DeBlock et al., *Plant Physiol.* 91, 691 (1989); Fromm et al., *BioTechnology* 8, 833 (1990); Gordon-Kamm et al., *Plant Cell* 2, 603 (1990). For example, resistance to glyphosphate or sulfonylurea herbicides has been obtained using genes coding for the mutant target enzymes, 5-enolpyruvylshikimate-3-phosphate synthase (EPSPS) and acetolactate synthase (ALS). Resistance to glufosinate ammonium, boromoxynil, and 2,4-dichlorophenoxyacetate (2,4-D) have been obtained by using bacterial genes encoding phosphinothricin acetyltransferase, a nitrilase, or a 2,4-dichlorophenoxyacetate monooxygenase, which detoxify the respective herbicides.

Selectable marker genes include, but are not limited to, genes encoding: neomycin phosphotransferase II (Fraley et al., *CRC Critical Reviews in Plant Science* 4, 1 (1986)); cyanamide hydratase (Maier-Greiner et al., *Proc. Natl. Acad. Sci. USA* 88, 4250 (1991)); aspartate kinase; dihydrodipicolinate synthase (Perl et al., *BioTechnology* 11, 715 (1993)); bar gene (Toki et al., *Plant Physiol.* 100, 1503 (1992); Meagher et al., *Crop Sci.* 36, 1367 (1996)); tryptophane decarboxylase (Goddijn et al., *Plant Mol. Biol.* 22, 907 (1993)); neomycin phosphotransferase (NEO; Southern et al., *J. Mol. Appl. Gen.* 1, 327 (1982)); hygromycin phosphotransferase (HPT or HYG; Shimizu et al., *Mol. Cell. Biol.* 6, 1074 (1986)); dihydrofolate reductase (DHFR); phosphinothricin acetyltransferase (DeBlock et al., *EMBO J.* 6, 2513 (1987)); 2,2-dichloropropionic acid dehalogenase (Buchanan-Wollatron et al., *J. Cell. Biochem.* 13D, 330 (1989)); acetohydroxyacid synthase (U.S. Pat. No. 4,761,373 to Anderson et al.; Haughn et al., *Mol. Gen. Genet.* 221, 266 (1988)); 5-enolpyruvyl-shikimate-phosphate synthase (aroA; Comai et al., *Nature* 317, 741 (1985)); haloarylnitrilase (WO 87/04181 to Stalker et al.); acetyl-coenzyme A carboxylase (Parker et al., *Plant Physiol.* 92, 1220 (1990)); dihydropteroate synthase (sulI; Guerineau et al., *Plant Mol. Biol.* 15, 127 (1990)); and 32 kDa photosystem II polypeptide (psbA; Hirschberg et al., *Science* 222, 1346 (1983)).

Also included are genes encoding resistance to: chloramphenicol (Herrera-Estrella et al., *EMBO J.* 2, 987 (1983)); methotrexate (Herrera-Estrella et al., *Nature* 303, 209 (1983); Meijer et al., *Plant Mol. Biol.* 16, 807 (1991)); hygromycin (Waldron et al., *Plant Mol. Biol.* 5, 103 (1985); Zhijian et al., *Plant Science* 108, 219 (1995); Meijer et al., *Plant Mol. Bio.* 16, 807 (1991)); streptomycin (Jones et al., *Mol. Gen. Genet.* 210, 86 (1987)); spectinomycin (Bretagne-Sagnard et al., *Transgenic Res.* 5, 131 (1996)); bleomycin (Hille et al., *Plant Mol. Biol.* 7, 171 (1986)); sulfonamide (Guerineau et al., *Plant Mol. Bio.* 15, 127 (1990); bromoxynil (Stalker et al., *Science* 242, 419 (1988)); 2,4-D (Streber et al., *Bio/Technology* 7, 811 (1989)); phosphinothricin (DeBlock et al., *EMBO J.* 6, 2513 (1987)); spectinomycin (Bretagne-Sagnard and Chupeau, *Transgenic Research* 5, 131 (1996)).

The bar gene confers herbicide resistance to glufosinate-type herbicides, such as phosphinothricin (PPT) or bialaphos, and the like. As noted above, other selectable markers that could be used in the vector constructs include, but are not limited to, the pat gene, also for bialaphos and phosphinothricin resistance, the ALS gene for imidazolinone resistance, the HPH or HYG gene for hygromycin resistance, the EPSP synthase gene for glyphosate resistance, the Hm1 gene for resistance to the Hc-toxin, and other selective agents used routinely and known to one of ordinary skill in the art. See generally, Yarranton, *Curr. Opin. Biotech.* 3, 506 (1992); Chistopherson et al., *Proc. Natl. Acad. Sci. USA* 89, 6314 (1992); Yao et al., *Cell* 71, 63 (1992); Reznikoff, *Mol. Microbiol.* 6, 2419 (1992); Barkley, et al., *The Operon* 177–220 (1980); Hu et al., *Cell* 48, 555 (1987); Brown et al., *Cell* 49, 603 (1987); Figge et al., *Cell* 52, 713 (1988); Deuschle et al., *Proc. Natl. Acad. Sci. USA* 86, 5400 (1989); Fuerst et al., *Proc. Natl. Acad. Sci. USA* 86, 2549 (1989); Deuschle et al., *Science* 248, 480 (1990); Labow et al., *Mol. Cell. Biol.* 10, 3343 (1990); Zambretti et al., *Proc. Natl. Acad. Sci. USA* 89, 3952 (1992); Baim et al., *Proc. Natl. Acad. Sci. USA* 88, 5072 (1991); Wyborski et al., *Nuc. Acids Res.* 19, 4647 (1991); Hillenand-Wissman, *Topics in Mol. And Struc. Biol.* 10, 143 (1989); Degenkolb et al., *Antimicrob. Agents Chemother.* 35, 1591 (1991); Kleinschnidt et al., *Biochemistry* 27, 1094 (1988); Gatz et al., *Plant J.* 2, 397 (1992); Gossen et al., *Proc. Natl. Acad. Sci. USA* 89, 5547 (1992); Oliva et al., *Antimicrob. Agents Chemother.* 36, 913 (1992); Hlavka et al., Handbook of Experimental Pharmacology 78, (1985); and Gill et al., *Nature* 334, 721 (1988). The disclosures described herein are incorporated by reference.

The above list of selectable marker genes are not meant to be limiting. Any selectable marker gene can be used in the present invention.

In view of the foregoing, it is apparent that one aspect of the present invention are transformed plant cells comprising the modified minimal or full-length promoter of the present invention. "Transformation", as defined herein, describes a process by which heterologous or homologous nucleic acid enters and changes a recipient cell. It may occur under natural or artificial conditions using various methods well known in the art. Transformation may rely on any known method for the insertion of foreign nucleic acid sequences into a eukaryotic host cell. Such "transformed" cells include stably transformed cells in which the inserted DNA is capable of replication either as an autonomously replicating plasmid or as part of the host chromosome. They also include cells which transiently express the inserted DNA or RNA for limited periods of time.

In a preferred embodiment of the invention, recipient cells for transformation are plant cells, preferably monocot plant cells, more preferably dicot plant cells, even more preferably Arabidopsis species plant cells, and most preferably *Arabidopsis thaliana* plant cells. "Plant cells" as used herein includes plant cells in plant tissue or plant tissue and plant cells and protoplasts in culture. Plant tissue includes differentiated and undifferentiated tissues of plants, including but not limited to, roots, shoots, leaves, pollen, seeds, tumor tissue and various forms of cells in culture, such as single cells, protoplasts, embryos and callus tissue. The plant tissue may be in plant, or in organ, tissue or cell culture.

The recombinant DNA molecule carrying a structural gene under promoter control can be introduced into plant tissue by any means known to those skilled in the art. As novel means are developed for the stable insertion of foreign genes into plant cells and for manipulating the modified cells, skilled artisans will be able to select from such means to achieve a desired result. Means for introducing recombinant DNA into plant tissue include, but are not limited to, direct DNA uptake (Paszkowski, J. et al. (1984) *EMBO J.* 3,2717), electroporation (Fromm, M., et al. *Proc. Natl. Acad. Sci. USA* 82,5824 (1985), microinjection (Crossway, A. et al. *Mol. Gen. Genet.* 202, 179 (1986)). or T-DNA mediated transfer from *Agrobacterium tumefaciens* to the plant tissue, which techniques are known in the art. There appears to be no fundamental limitation of T-DNA transformation to the natural host range of Agrobacterium. Representative T-DNA vector systems are described in the following references: An, G. et al. *EMBO J.* 4, 277 (1985); Herrera-Estrella, L. et al., *Nature* 303, 209 (1983); Herrera-Estrella, L. et al. *EMBO J.* 2, 987 (1983); Herrera-Estrella, L. et al. in *Plant Genetic Engineering*, New York: Cambridge University Press, p. 63 (1985). Once introduced into the plant tissue, the expression of the structural gene may be assayed by any means known to the art, and expression may be measured as mRNA transcribed or as protein synthesized, as provided herein.

Transgenic plants comprising the modified promoter of the present invention (as present, for example, in a DNA construct of the present invention, or a transformed cells of the present invention) are also an aspect of the present invention. Procedures for cultivating transformed cells to useful cultivars are known to those skilled in the art. Techniques are known for the in vitro culture of plant tissue, and in a number of cases, for regeneration into whole plants. A further aspect of the invention are plant tissue, plants or seeds containing the chimeric DNA sequences described above. Preferred are plant tissues, plants or seeds containing those chimeric DNA sequences which are mentioned as being preferred.

The transformed cells, identified by selection or screening and cultured in an appropriate medium that supports regeneration as provided herein, will then be allowed to mature into plants. Plants are preferably matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con®s. After the regenerating plants have reached the stage of shoot and root development, they may be transferred to a greenhouse for further growth and testing. Progeny may be recovered from the transformed plants and tested for expression of the exogenous expressible gene by localized application of an appropriate substrate to plant parts such as leaves.

The regenerated plants are screened for transformation by standard methods illustrated below. Progeny of the regenerated plants is continuously screened and selected for the continued presence of the integrated DNA sequence in order to develop improved plant and seed lines. The DNA sequence can be moved into other genetic lines by a variety of techniques, including classical breeding, protoplast fusion, nuclear transfer and chromosome transfer.

After effecting delivery of the promoter and heterologous DNA to recipient cells and plants by any of the methods discussed above, identifying the cells exhibiting successful or enhanced expression of a heterologous gene for further culturing and plant regeneration generally occurs. As mentioned above, in order to improve the ability to identify transformants, one may desire to employ a selectable or screenable marker gene as, or in addition to, the expressible gene of interest. In this case, one would then generally assay the potentially transformed cell population by exposing the cells to a selective agent or agents, or one would screen the cells for the desired marker gene.

"Screening" generally refers to identifying the cells exhibiting expression of a heterologous gene that has been transformed into the plant. Usually, screening is carried out to select successfully transformed seeds (i.e., transgenic seeds) for further cultivation and plant generation (i.e., for the production of transgenic plants). As mentioned above, in order to improve the ability to identify transformants, one may desire to employ a selectable or screenable marker gene as, or in addition to, the heterologous gene of interest. In this case, one would then generally assay the potentially transformed cells, seeds or plants by exposing the cells, seeds, plants, or seedlings to a selective agent or agents, or one would screen the cells, seeds, plants or tissues of the plants for the desired marker gene. For example, transgenic cells, seeds or plants may be screened under selective conditions, such as by growing the seeds or seedlings on media containing selective agents, such as antibiotics (e.g., hygromycin, kanamycin, paromomycin or BASTA®), the successfully transformed plants having been transformed with genes encoding resistance to such selective agents.

To additionally confirm the presence of the heterologous nucleic acid or "transgene(s)" in the seeds of the cultivated plant or the in the regenerated plants produced from those seeds, a variety of assays may be performed. Such assays include, for example, molecular biological assays, such as Southern and Northern blotting and PCR; biochemical assays, such as detecting the presence of a protein product, e.g., by immunological means (ELISAs and Western blots) or by enzymatic function; by plant part assays, such as leaf or root assays; and also, by analyzing the phenotype of the whole regenerated plant.

While Southern blotting and PCR may be used to detect the gene(s) in question, they do not provide information as to whether the gene is being expressed. Expression of the heterologous gene may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these techniques are among the most commonly employed, other procedures are known in the art and may be additionally used.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these techniques are among the most commonly employed, other procedures are known in the art and may be additionally used.

Plant parts include attached or detached portions of a plant, including leaves, stems, roots, flowers, fruits or parts thereof.

The term "restriction site" refers to a deoxyribonucleic acid sequence at which a specific restriction endonuclease cleaves the plasmid, vector or DNA molecule.

The mininal promoter is the minimal element necessary for transcription i.e. "reading" a selected or specified gene of DNA and preparing the mRNA "message" from the gene by RNA polymerase. The minimal promoter can be used to create a chimeric gene. For example, an Upstream Activating Sequence (UAS) such as 4×Gal4, can be placed upstream of the minimal promoter, and a structural gene such as the β-glucuronidase (GUS) can be placed downstream. In the present invention, transcription or "reading" of the GUS gene can be activated if a specific trans-activator protein such as Gal4-2×VP16 is present. This trans-activator consists of a Gal4 DNA binding domain and a 2×VP16 activation domain, the first which binds to the UAS, the latter which initiates "reading" of the structural gene.

The chimeric gene can then be transformed into a plant by any practicable method. In the transformed plant, the promoter can confer high level of transcription of the downstream nucleotide sequence or the contiguous structural coding sequences in meristematic tissues and/or regions of rapidly dividing cells in the plant. Also, the promoter can confer a high level of transcription in other plant cells that do not divide or divide slowly.

For the modified minimal promoter, a structural gene such as the GUS gene, which is located downstream of the MMP and the UAS, will not be transcribed (i.e. the construct will be silent) unless a specific trans-activation protein, such as Gal4-2×VP16, is present. The gene coding for this chimeric trans-activator is located on a separate plasmid construct and is under control of a constitutive promoter. Only when both constructs are present in a cell, a structural gene such as the GUS gene, placed downstream of the UAS and MMP, gets transcribed. The functionality of the MMP can be tested via transactivation using:

a) Transactivation by transient expression of both genes (ie. the silent GUS gene and the transactivator) in rice suspension cells using particle bombardment (Example 4)

b) Transactivation by combining the two genes by crossing two plants, each containing one of the transgenes in rice (*Oryza sativa*), using particle bombardment for plant transformation (Example 5).

c) Transactivation by combining the two genes by crossing two plants, each containing one of the transgenes in *Arabidopsis thaliana*, using Agrobacterium-mediated plant transformation (Example 6).

A diagram showing the procedure for cloning the modified minimal promoter into a suitable DNA construct and insertion or transformation into plants or plant tissue is shown in FIG. 1.

The sequence for the modified minimal promoter and/or the modified full-length promoter is generally based upon modifications of the consensus and other sequences of promoters from plant DNA viruses, such as the figwort mosaic virus (FMV) and the cauliflower mosaic virus (CaMV). Once the DNA sequence of the minimal promoter and/or the full-length promoter is determined, its two complementary single strands can be individually synthesized using established techniques by having the strands prepared by a commercial vendor.

For the modified minimal promoter, the two complementary oligonucleotide strands containing the desired nucleotide sequences can be annealed (i.e. brought together) to form the modified minimal promoter (MMP). The minimal promoter, built from the annealed oligonucleotides, has the necessary sequence context and phosphorylation to be cloned into a vector or plasmid having PstI- or PmeI-restriction sites, respectively. The minimal promoter (the annealed strands) are inserted into pPG344 plasmid vector together with single (1×) or multiple copies (two to ten or more copies designated as 2×, 3×, 4×, 5× and 10×) of Gal4 (i.e. 4×Gal4) upstream activating sequence (UAS) to form a first intermediate pPG345 plasmid vector. A structural gene (i.e. the GUS gene from plasmid vector pPG347) is joined or inserted into first intermediate pPG345 plasmid vector to yield the vector or plasmid pPG346 containing the desired modified minimal promoter downstream of the upstream activating sequences and upstream of the GUS gene and the Ag7 terminator (4×Gal4UAS-MMP-GUS-Ag7).

"Upstream Activating Sequence" refers to four or more copies of a Gal4 upstream activation sequence from *Saccharomyces cerevisiae*, as described by Schwechheimer et al. in 1998 (Plant Mol Biol 36: 195–204). The Gal4 DNA-binding domain of the trans-activator protein Gal4-2×VP16 binds to this DNA sequence, which is located directly upstream of the minimal promoter.

In order to insert the desired gene containing the modified minimal promoter into a plant cell, plasmid pPG346 is used for direct gene transfer to plants, such as transfer of the plasmid to the plant cell by particle bombardment using a gene gun. In the case of particle bombardment, plasmid constructs pPG352 (examples 4 and 5) or pPG354 (example 5) are also used for trans-activation (pPG352) of the silent gene containing the modified minimal promoter or for selection of the transformed cells (pPG354). Alternatively, the gene containing the modified minimal promoter is cloned from pPG346 into a binary vector, e.g. pPG348 (also known as a T-DNA plasmid), to yield pPG349. This vector is inserted into a suitable strain of bacteria such as Agrobacterium, such as *Agrobaceterium tumefaciens* strain LBA4404. Once the vector is inside, Agrobacterium can be co-incubated with plant cells. The Agrobacterium then transfers the desired gene containing the modified minimal promoter into the plant cell, where it will be integrated into the plant genome and subsequently expressed upon presence of a trans-activator, such as Gal4-2×VP16. The following Examples are provided to illustrate the present invention, and should not be construed as limiting thereof.

EXAMPLE 1

Preparation of a minimal promoter with a PstI sticky end and a PmeI blunt end in the annealed, double-stranded molecules.

The DNA sequence of the first sequence (polynucleotide 1) is as follows:

5'-GTCCTCTATATAAGGAGGGGTTCATTC-CCATTTGAAGGATCAATAGTTT-3' [SEQ ID NO: 7]

The DNA sequence of the second strand (polynucleotide 2) is as follows:

5'-AAACTATTGATCCTTCAAATGGGAAT-GAACCCCTCCTTATATAGAGGACTGCA-3' [SEQ ID NO:9]

The following is a representation of the DNA sequence for the annealed polynucleotides i.e. double stranded minimal promoter, wherein the non-bold portions of the strands make up the cloning sites:

5'-GTCCTCTATATAAGGAGGGGTTCATTC-CCATTTGAAGGATCAATAGTTT-3' [SEQ ID NO: 7]

3'-ACGTCAGGAGATATATTCCTCCCCAAG-TAAGGGTAAACTTCCTAGTTATCAAA-5' [SEQ ID NO:9]

The minimal promoter is a fragment of DNA having a modified sequence (i.e. non-naturally occurring) and can be prepared using methods described hereinbefore. For example, the sequence of nucleotides in the DNA of a double-stranded minimal promoter having 49 and 53 nucleotides in each sequence or strand is determined. Each DNA sequence is chemically synthesized with a modified ABI 391 synthesizer which employs standard β-cyano-ethyl chemistry. Each polynucleotide strand is phosphorylated at its 5'-ends. The two polynucleotides strands (polynucleotide 1 and polynucleotide 2) are substantially complementary copies of each other and form a double stranded (ds) minimal promoter when annealed together. In addition, both polynucleotides contain additional nucleotides at their 5'- and 3'-ends, in order to create the required sequence context, that, after ligation to a cloning vector such as pPG344 that has been digested with the restriction enzymes PstI (at 5'-end) and PmeI (at 3'-end), the PstI and PmeI sites in the cloning vector are restored. With these additional nucleotides and the phosphorylation, the annealed minimal promoter (in an isolated form) can be cloned directly into a vector that has been digested with PstI and PmeI restriction enzymes.

The annealing of the two polynucleotide is performed as follows. The desiccated polynucleotide are dissolved at high concentration (10 $OD_{260}$ units/100 ul) in STE buffer (5 mM NaCl, 10 mM Tris pH 8.0, 1 mM EDTA). Equal volumes (25 ul each) are mixed in a 1.5 ml centrifuge tube and heated in a water bath to 94° C., then slowly cooled down to room temperature over about 2 hours by "unplugging" the water bath (i.e., by allowing the water bath to reach room temperature naturally). The DNA is precipitated by adding 0.5 volumes (25 ul) 7.5 M ammonium acetate and 2 μl 1M $MgCl_2$ and 125 μl ethanol, mixing, incubating at 4° C. for 12 hours, and centrifuging for 15 minutes at room temperatures at 14'000 rpm. The DNA pellet is washed once with 500 ul of 70% ethanol, then air-dried and resuspended in 100 ul TE (10 mM Tris pH8.0, 1 mM EDTA). Annealing of the two polynucleotides yields the nucleotide sequence provides above as the double stranded minimal promoter.

EXAMPLE 2

Figure 2:
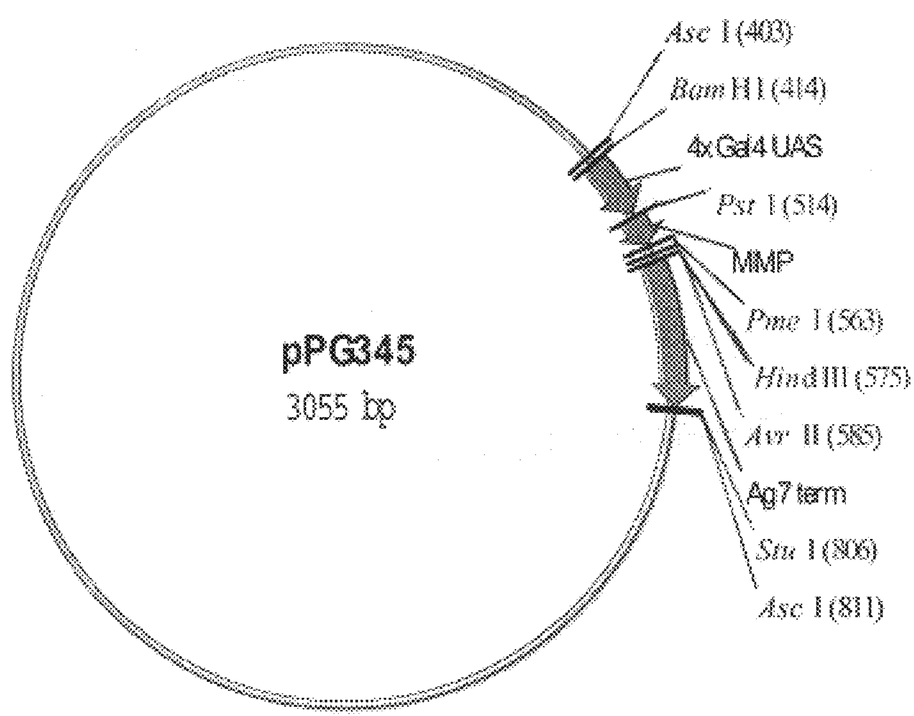
FIG. 2 is a diagram of plasmid pPG345.

Preparation of plasmid construct pPG345 containing the 4×Gal4 UAS, the modified minimal promoter (MMP) and the Ag7 terminator. Plasmid pPG345 is shown in FIG. 2. Plasmid vector pPG345 is derived from pPG344 and consists of 3055 basepairs. pPG345 is set forth as follows, wherein AscI, BamHI, PstI, PmeI, HindIII, AvrII, StuI, are restriction enzyme sites (numbers in parentheses indicate the nucleotide positions where the respective restriction enzyme cuts the DNA sequence), 4×Gal4UAS is DNA sequence containing four copies of a Gal4 upstream activation sequence from *Sacchoromyces cerevisiae*, as described hereinbefore, MMP is the modified minimal promoter, and Ag7 term is as described hereinafter for pPG344.

The Ag7 terminator is derived from the starting plasmid vector pPG344. The upstream activating sequence 4×Gal4 UAS contains four copies of a Gal4 upstream activation sequence from *Sacchoromyces cerevisiae*, as described by Schwechheimer et al. in 1998 (Plant Mol Biol 36: 195–204) and includes BamHI and PstI sites for cloning the sequence into plasmid vector pPG344. The upstream activating sequence 4×Gal4 UAS (including BamHI and PstI restriction sites) can be represented by its nucleotide sequence as follows:

5'-GGATCCGGAAGACTCTCCTCCGAGATC-CGGAAGACTCTCCTCCGAGATCCGGAA-GACTCTCCTCCGAGATCCGGAA-GACTCTCCTCCGAGATCCCCCTGCAG-3'

The construction of plasmid vector pPG345, starting from plasmid vector pPG344 can be described as follows: 500 nanograms of the plasmid vector pPG344 (starting material), comprising the vector backbone and the Ag7 terminator, are digested with the restriction enzymes BamHI and PmeI (New England Biolabs) and the linearized plasmid vector pPG344, with digested BamHI and PmeI sites is isolated following common laboratory protocols that are known to those skilled in the art (such as Sambrook et al. 1989, *Molecular Cloning: A Laboratory Manual*).

In a ligation reaction, the following DNA pieces are ligated together: 1) Plasmid vector pPG344 digested with BamHI and PmeI, as described above, 2) Modified minimal promoter (MMP) with PstI and PmeI sites as described above, 3) A piece of double stranded DNA comprising four copies of the Gal4 upstream activating sequence (4×Gal4 UAS) and BamHI and PstI restriction sites at the 5'-, or 3'-end, respectively. Before ligation, the 4×Gal4 UAS was digested with the restriction enzymes BamHI and PstI, following common laboratory protocols that are known to those skilled in the art. The ligation is performed following common laboratory protocols that are known to those skilled in the art (such as Sambrook et aL 1989, *Molecular Cloning: A Laboratory Manual*), yielding plasmid vector pPG345.

EXAMPLE 3

Figure 3:
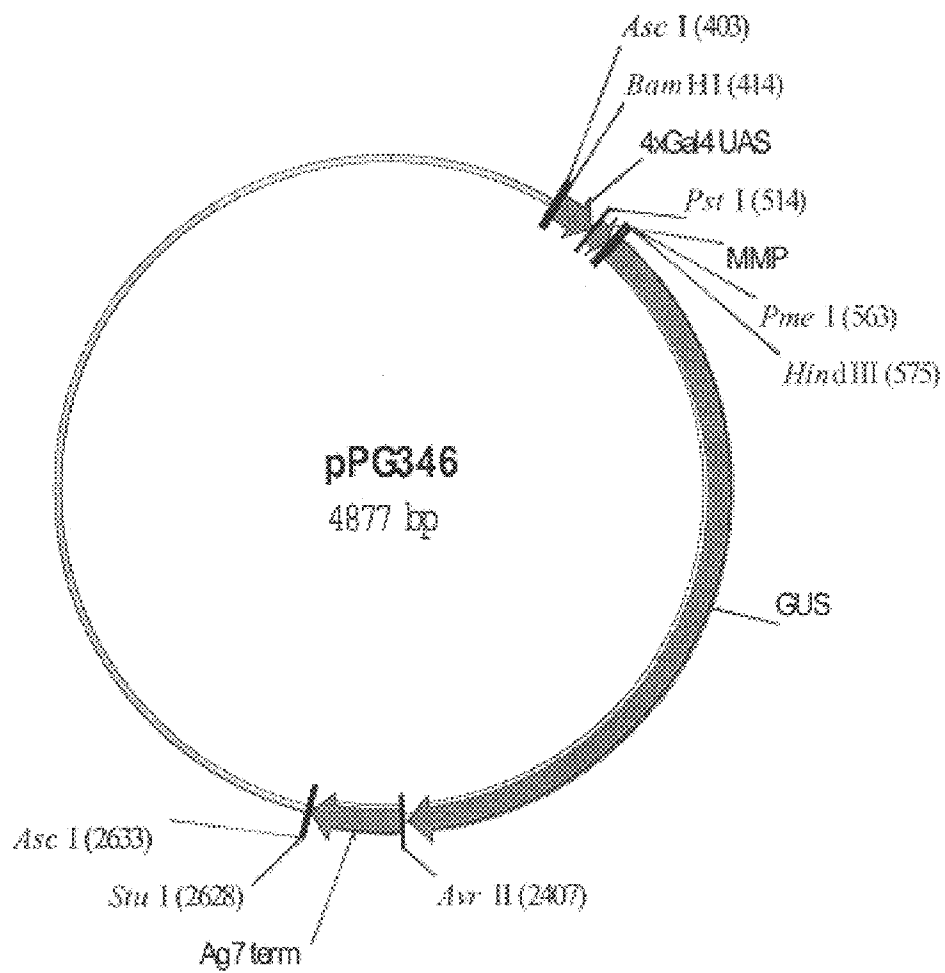
FIG. 3 is a diagram of plasmid pPG346.

Preparation of plasmid construct pPG346 containing a structural gene (i.e. the β-glucuronidase (GUS) gene) with the modified minimal promoter. Plasmid pPG346 is shown in FIG. 3. The plasmid vector pPG346 is derived from pPG345 and consists of 4877 basepairs. pPG346 is set forth as follows, wherein AscI, BamHI, PstI, PmeI, HindIII, AvrII, StuI, are restriction enzyme sites (numbers in parentheses indicate the nucleotide positions where the respective restriction enzyme cuts the DNA sequence). 4×Gal4UAS is DNA sequence containing four copies of a Gal4 upstream activation sequence from *Sacchoromyces cerevisiae*, as described hereinbefore, MMP is the modified minimal promoter, GUS (β-glucuronidase) is the structural gene as described hereinafter for pPG347, and Ag7 term is as described hereinafter for pPG344.

The GUS gene is inserted into plasmid construct pPG345 from plasmid construct pPG347. The GUS gene is excised from pPG347 as a HindIII/AvrII fragment, and plasmid pPG345 containing the 4×Gal4 UAS, the modified minimal promoter (MMP), and the Ag7 terminator is digested with HindIII and AvrII restriction enzymes. The two pieces of DNA (i.e. the HindIII/AvrII-GUS gene fragment and the with HindIII and AvrII restriction enzymes linearized plasmid construct pPG345) are ligated together to yield plasmid construct pPG346. Restriction digests and ligation reactions are performed following common laboratory protocols that are known to those skilled in the art (such as Sambrook et al. 1989*, Molecular Cloning: A Laboratory Manual*).

EXAMPLE 3a

Figure 4:
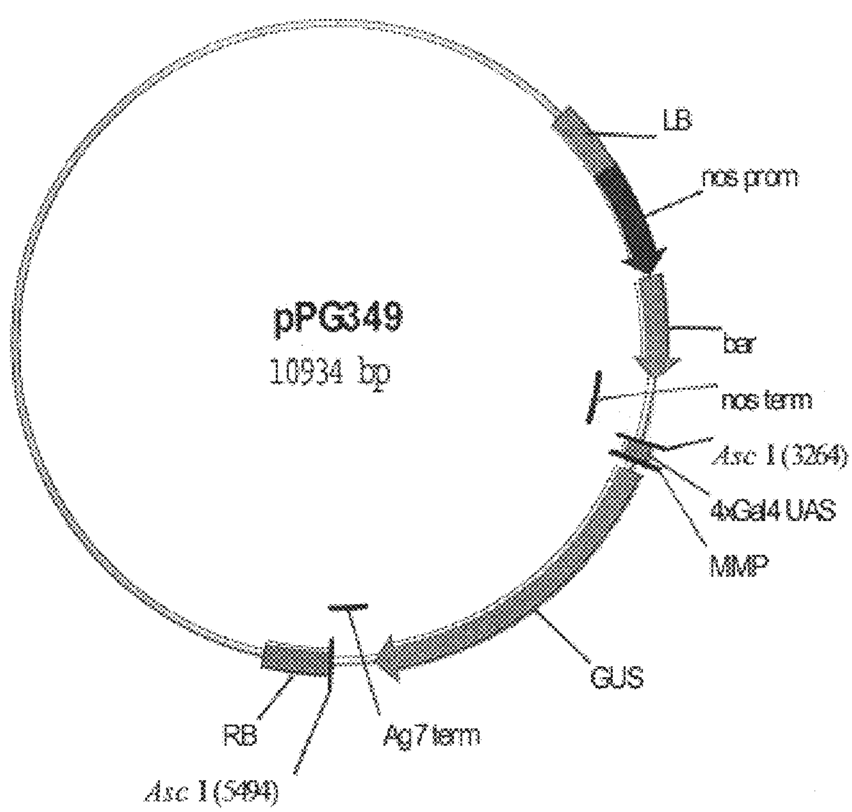
FIG. 4 is a diagram of plasmid pPG349.

Preparation of pPG349, a binary vector for Agrobacterium-mediated transformation that consists of 10934 basepairs. Plasmid pPG349 is shown in FIG. 4. For construction of the binary vector pPG349, both plasmid construct pPG346 and binary vector pPG348 are digested with restriction enzyme AscI and the part of pPG346 containing the heterologous gene 4×Gal4UAS-MMP-GUS-Ag7 is ligated into linearized binary vector pPG348, to yield binary vector pPG349, containing the heterologous gene 4×Gal4UAS-MMP-GUS-Ag7. Restriction digests and ligation reactions are performed following common laboratory protocols that are known to those skilled in the art (such as Sambrook et al. 1989*, Molecular Cloning: A Laboratory Manual*). pPG349 is set forth as follows, wherein AscI is a restriction enzyme site (the number in parentheses indicates the nucleotide position where AscI cuts the DNA sequence). LB and RB are as described hereinafter for pPG348, nos prom, bar and nos term are as described hereinafter for pPG348, 4×Gal4UAS, MMP, GUS and Ag7 term are as described hereinbefore for pPG346.

EXAMPLE 4

Functional test of the modified minimal promoter (MMP) in a transient expression system: Transfer of two plasmid vectors, each containing one gene (i.e. pPG346 containing the heterologous gene 4×Gal4UAS-MMP-GUS-Ag7 and pPG 352, containing a gene for the trans-activator protein Gal4-2×VP16) to rice suspension cells and subsequent transient expression of the two genes in the rice suspension cells. The plasmid vectors are delivered to the rice suspension cells by particle bombardment. Only if the modified minimal promoter fulfills the function of a minimal promoter, the GUS gene can be transcribed upon trans-activation by the trans-activator protein Gal4-2×VP16.

Rice suspension cells are used for transformation that have been obtained basically as described by Chen et al. in 1998 (Plant Cell Rep 18: 25–31). Mature rice seeds of the variety TP309 are surface sterilized and then plated on callus induction medium. After 3 days, the embryos are isolated and further incubated on callus induction medium. After 2 weeks, calli grown from the embryos are transferred to liquid medium and are incubated on a shaker. The calli are subcultured weekly, always selecting the smallest callus pieces for further cultivation. The callus is used for transformation starting after 4 weeks after callus initiation.

For the transfer of the plasmids into the rice suspension cells, a particle inflow gun and a modified protocol is used as described in Finer et al. in 1992 (Plant Cell Rep 11: 323–328). Basically, suspension calli are transferred to semi-solid high-osmoticum callus induction medium containing 100 grams per liter sucrose. After 2 hours, the calli are bombarded with a gold particle suspension with both plasmids pPG346 and pPG352 mixed together at equal amounts (i.e. 2.5 ug of both plasmids are precipitated to 5 micrograms of gold particles and 1/10 of that mixture is used for bombardment). After bombardment, the calli are incubated for 2 days on the high osmoticum medium before analysis of transient gene expression.

The analysis of GUS gene expression is performed using a modified protocol as described by Jefferson in 1987 (Plant Mol Biol Rep 5: 387–405). The bombarded calli are transferred to histological GUS staining solution containing 0.1 M K/Na-phosphate pH 7.0, 10 mM Na-EDTA, 0.1% Triton X-100, 5 mM Potassium ferricyanide (III), 5 mM Potassium ferrocyanide (II), and 100 mg X-Gluc (5-Bromo-4-chloro-3-indolyl-beta-D-glucuronide acid cyclohexylammoniumsalt). The immersed calli are incubated in the staining solution at 37° C. for 16 hours. The incubated calli are observed using a stereomicroscope. Blue stained cells indicate expression of the GUS gene, and therefore a functional MMP.

EXAMPLE 5

Production of transgenic rice plants containing the modified minimal promoter (MMP) and testing the function of the MMP in the transgenic rice plants. Plasmid construct pPG346, containing the heterologous gene 4×Gal4UAS-MMP-GUS-Ag7, is transferred to rice cells, transgenic rice cells are selected and from these transgenic rice cells, transgenic rice plants are regenerated. For selection of transgenic rice cells, plasmid construct pPG354, containing a hygromycin resistance gene which allows selection of transgenic cells with the antibiotic hygromycin B (as described in “Starting Materials”), is co-transformed to the rice cells. Transgenic rice plants containing the heterologous gene 4×Gal4UAS-MMP-GUS-Ag7 from plasmid construct pPG346 are subsequently crossed with transgenic rice plants, containing a heterologous transgene coding for a trans-activator, such as Gal4-2×VP16 (i.e. as in plasmid construct pPG352, as described in “Starting Materials”). All plasmid vectors are transferred to rice suspension cells by particle bombardment. The activity of the GUS gene is subsequently tested in the progeny plants of such a cross. Progeny plants of such a cross, which contain both transgenes (i.e. the heterologous gene 4×Gal4UAS-MMP-GUS-Ag7 from plasmid construct pPG346 and the heterologous transgene coding for the trans-activator protein Gal4-2×VP16 from plasmid construct pPG352) express the GUS gene. Only if the modified minimal promoter fulfills the function of a minimal promoter, the GUS gene can be transcribed upon trans-activation by the trans-activator protein Gal4-2×VP16. The following is a description of production of transgenic rice plants containing the transgene from pPG346 (i.e. the heterologous gene 4×Gal4UAS-MMP-GUS-Ag7), subsequent crossing of such a transgenic rice plant to an other transgenic rice plant containing the gene from pPG352 (i.e. the heterologous transgene coding for the trans-activator protein Gal4-2×VP16), and analysis of the GUS expression in the progeny plants of such a cross, which contain both the transgenes.

Rice suspension cells are bombarded as described in example 4, with pPG346 and pPG354 co-bombarded. After bombardment, the calli are cultured using a modified protocol as described by Burkhardt et al. in 1997 (Plant J 11: 1071–1078). Basically, one day after bombardment the bombarded calli are transferred to selective callus initiation medium containing 50 milligram per liter hygromycin B and are incubated for 4 weeks. Resistant calli growing on this medium are transferred to fresh selection medium for one week. Embryogenic calli are transferred to regeneration medium and regenerated plants are first transferred to rooting medium, later to soil. The presence of the GUS transgene in the transgenic plants is verified by Southern analysis using standard laboratory protocols as described in Potrykus and Spangenberg (Eds.) in 1995 (Gene Transfer to Plants. Springer-Verlag, Berlin Heidelberg, pp 221–228) using a radioactive labeled probe spanning the complete GUS gene. At flowering stage, the verified transgenic plants are crossed to transgenic rice plants containing the gene for the transactivator protein (i.e. the heterologous transgene coding for the trans-activator protein Gal4-2×VP16 from pPG352). For the crosses, flowers of the plants derived from bombardment are demasculinated before anthesis and pollinated with pollen from the plants which contain the transactivator transgene, following protocols known to those skilled in the art. Then, the plants are grown to maturity and seeds from the cross-pollinated flowers are collected. For detection of the transactivation of the GUS gene in the progeny plants, the seeds derived from the cross-pollinated flowers are surface sterilized with 6% calcium hypochlorite for 10 minutes, rinsed with sterile distilled water and germinated on semi-solid agarose medium, containing half strength MS salts and vitamins (Sigma, M-5519), 20 grams per liter sucrose and 3.5 grams per liter agarose (pH 5.6). Five days after germination seedlings are immersed in GUS staining solution as described hereinbefore, and vacuum infiltrated for 5 minutes at 75 mmHg. GUS expression in the seedlings which contain both transgenes is detected by observing the incubated seedlings, or cross-sections thereof, under a stereomicroscope. Blue stained cells indicate expression of the GUS gene.

EXAMPLE 6

Production of transgenic *Arabidopsis thaliana* plants containing the modified minimal promoter (MMP) and testing the function of the MMP in the transgenic *Arabidopsis thaliana* plants. Binary vector pPG349, containing the heterologous gene 4×Gal4UAS-MMP-GUS-Ag7, is transferred to a *Agrobacterium tumefaciens* strain (i.e. *Agrobacterium tumefaciens* strain LBA4404) and the T-DNA, containing the heterologous gene 4×Gal4UAS-MMP-GUS-Ag7 from binary construct pPG349 is subsequently transferred by the Agrobacterium to cells from *Arabidopsis thaliana*. Transgenic *Arabidopsis thaliana* plants containing the heterologous gene 4×Gal4UAS-MMP-GUS-Ag7 from binary construct pPG349 are selected and subsequently crossed with transgenic *Arabidopsis thaliana* plants, containing a heterologous transgene coding for a trans-activator, such as Gal4-2×VP16 (i.e. as in binary construct pPG353, as described in "Starting Materials"). The activity of the GUS gene is subsequently tested in the progeny plants of such a cross. Progeny plants of such a cross, which contain both transgenes (i.e. the heterologous gene 4×Gal4UAS-MMP-GUS-Ag7 from binary construct pPG349 and the heterologous transgene coding for the trans-activator protein Gal4-2×VP16 from binary construct pPG353) express the GUS gene. Only if the modified minimal promoter fulfills the function of a minimal promoter, the GUS gene can be transcribed upon trans-activation by the trans-activator protein Gal4-2×VP16.

The following is a description of production of transgenic *Arabidopsis thaliana* plants containing the transgene from pPG349 (i.e. the heterologous gene 4×Gal4UAS-MMP-GUS-Ag7), subsequent crossing of such a transgenic *Arabidopsis thaliana* plant to an other transgenic *Arabidopsis thaliana* plant containing the T-DNA from binary vector pPG353 (i.e. the heterologous transgene coding for the trans-activator protein Gal4-2×VP16), and analysis of the GUS expression in the progeny plants of such a cross, which contain both the transgenes.

Transgenic *Arabidopsis thaliana* plants containing the T-DNA from binary vector pPG349 are produced using the floral dip method as described by Clough et al. in 1998 (Plant J 16: 735–743). Basically, plants are grown in soil until the primary inflorescence is about 10 cm tall. The primary inflorescence is cut to induce the emergence of multiple secondary inflorescences. The inflorescences of these plants are dipped in a suspension of *Agrobacterium tumefaciens*, strain LBA4404, containing the binary vector pPG349. After the dipping process, the plants are grown to maturity and the seeds are harvested. Transgenic seeds from these treated plants are selected by germination in soil and subsequent spraying with the chemical bialaphos (i.e. as contained in "Liberty", diluted 1:5000) on three consecutive days after the first true leaves of the plants have emerged. Transgenic plants containing the selectable "bar" marker gene (as described hereinafter in the description of pPG348 in "Starting Materials") survive this treatment and are transplanted to individual pots. At flowering stage, the selected transgenic plants are crossed to transgenic *Arabidopsis thaliana* plants containing the gene for the trans-activator protein (i.e. the heterologous transgene coding for the trans-activator protein Gal4-2×VP16 from pPG353). For the crosses, flowers of the selected plants containing the T-DNA from the binary construct pPG349 are demasculinated before anthesis and pollinated with pollen from the plants which contain the transactivator transgene, following protocols known to those skilled in the art. Then, the plants are grown to maturity and seeds from the cross-pollinated flowers are collected. For detection of the transactivation of the GUS gene in the progeny plants, the seeds derived from the cross-pollinated flowers are surface sterilized in chlorine gas as described by Ye et al. in 1999 (Plant J 19: 249–257) and germinated on semi-solid agarose medium, containing half strength MS salts and vitamins (Sigma, M-5519), 20 grams per liter sucrose and 3.5 grams per liter agarose (pH 5.6). Five days after germination seedlings are immersed in GUS staining solution as described hereinbefore, and vacuum infiltrated for 5 minutes at 75 mmHg. GUS expression in the seedlings which contain both transgenes is detected by observing the incubated seedlings under a stereomicroscope. Blue stained cells indicate expression of the GUS gene.

A heterologous gene such as a β-glucuronidase (GUS) gene, located downstream of the modified full-length promoter, and upstream of a terminator region such as the Ag7 terminator, can be transcribed and the resulting RNA can be translated when this heterologous gene is transferred to a plant cell, using any practicable method, such as particle bombardment or Agrobacterium-mediated transformation. The functionality of the modified full-length promoter can be tested by incubating transformed plant cells in a solution, containing a substrate which is converted into a blue product by the protein produced from the GUS gene. The functionality of the modified promoter can therefore be assessed by observing such transformed and incubated plant cells under a stereo microscope, screening for blue stained cells. Transgenic plants containing a structural gene, such as the GUS gene, downstream of the modified promoter, can be produced using any practicable method for plant transformation. Two methods are described herein later:

a) Transformation of rice tissue cells by particle bombardment and regeneration of transgenic rice plants containing the GUS gene under control of the modified promoter (Example 11).

b) Transformation of *Arabidopsis thaliana* plants by Agrobacterium-mediated transformation using the "flower dip" method and screening for transgenic *Arabidopsis thaliana* plants containing the GUS gene under control of the modified promoter (Example 12).

Figure 5:
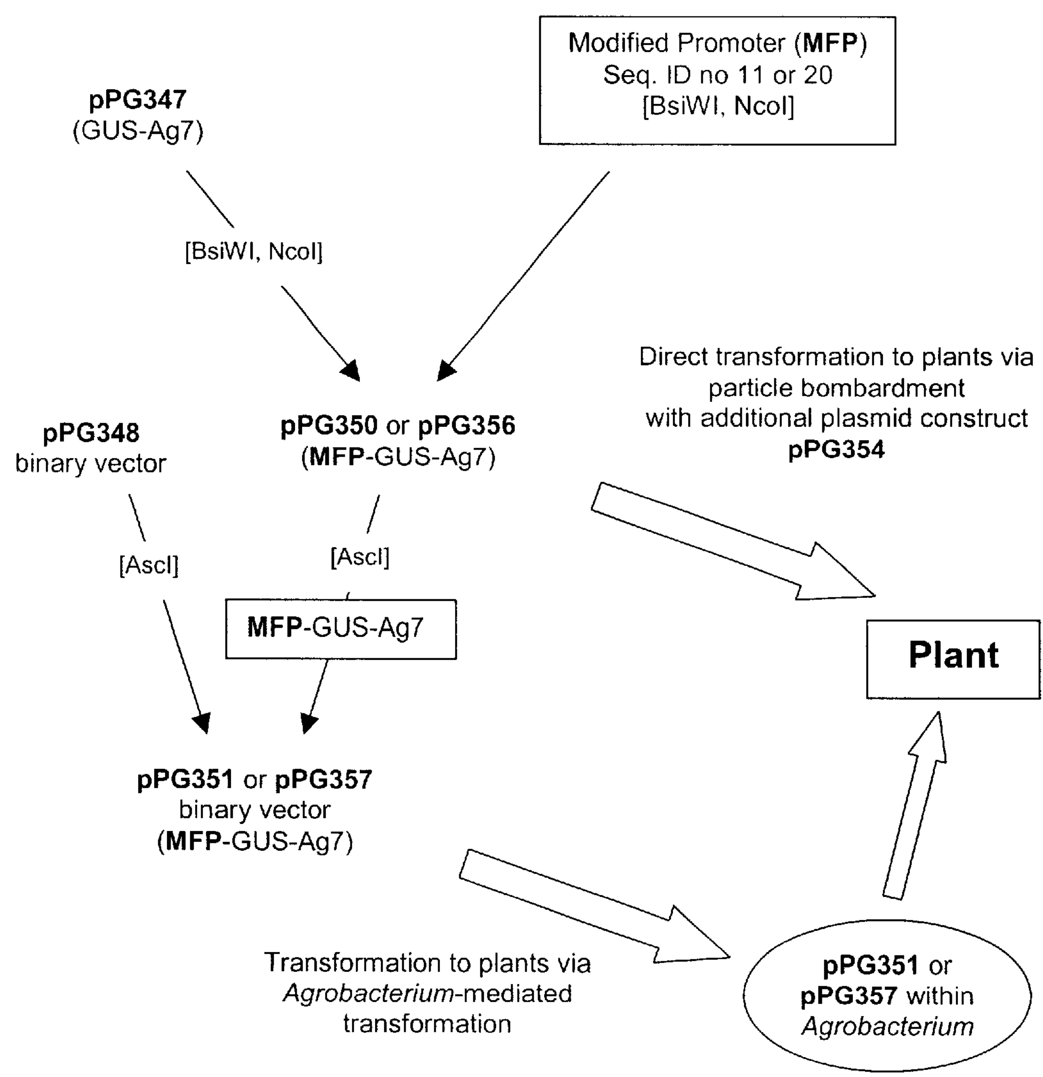
FIG. 5 is a diagram of the procedure for cloning of the full-length promoter into a suitable DNA construct and tranformation into plants or plant tissue.

A diagram showing the procedure for cloning the modified full-length promoter into a suitable DNA construct and insertion or tranformation into plants or plant tissue is shown in FIG. 5.

The sequence for the modified minimal promoter and/or the modified full-length promoter is generally based upon modifications of the consensus and other sequences of promoters from plant DNA viruses, such as the figwort mosaic virus (FMV) and the cauliflower mosaic virus (CaMV). Once the DNA sequence of the minimal promoter and/or the full-length promoter is determined, its two complementary single strands can be individually synthesized using established techniques by having the strands prepared by a commercial vendor.

For the modified full-length promoters, eight oligonucleotide strands, together forming the desired nucleotide sequences, can be annealed (i.e. brought together) to form a modified full-length promoter (MFP). The modified full-length promoters, built from the annealed oligonucleotides, has the necessary sequence context and phosphorylation to be cloned into a vector or plasmid having BsiWI- or NcoI-restriction sites, respectively. The modified full-length promoter (the annealed strands) is inserted into pPG347 plasmid vector, replacing the sequence for the CaMV35S promoter, to form pPG350 or pPG356 plasmid vector, respectively. Plasmid vectors pPG350 or pPG356 contain the desired modified full-length promoter upstream of the GUS gene and the Ag7 terminator (MFP-GUS-Ag7).

In order to insert the desired gene containing the modified full-length promoter into a plant cell, plasmid pPG350 or pPG356 are used for direct gene transfer to plants, such as transfer of the plasmid to the plant cell by particle bombardment using a gene gun. In the case of particle bombardment, plasmid construct pPG354 is also used for selection of the transformed cells. Alternatively, the gene containing the modified full-length promoter is cloned from pPG350 or pPG356 into a binary vector, e.g. pPG348 (also known as a T-DNA plasmid), to yield pPG351 or pPG357. These vectors are inserted into a suitable strain of bacteria such as Agrobacterium, such as *Agrobacterium tumefaciens* strain LBA4404. Once the vector is inside, Agrobacterium can be co-incubated with plant cells. The Agrobacterium then transfers the desired gene containing the modified full-length promoter into the plant cell, where it will be integrated into the plant genome and subsequently expressed.

EXAMPLE 7

Preparation of a full-length prmoter. A full-length pronoter [SEQ ID NO: 11] can be prepared by annealing together eight synthetic polynucleotides [SEQ ID NO: 12–19]. To anneal the eight polynucleotides, dessicated polynucleotides are dissolved at high concentration (10 $OD_{260}$ units/100 $\mu$l (microliters)) in STE buffer (50 mM (micromolar) NaCl, 10 mM Tris pH 8.0, 1.0 mM (millimolar) ethylene diamine tetracetic acid (EDTA)). Equal volumes (12 $\mu$l each) are mixed in a 1.5 milliliter (ml) centrifuge tube and heated in a water bath to 94° C., then slowly cooled down to room temperature over a three hour period by slowly draining or unplugging the water bath. The DNA is precipitated by adding 0.5 volumes (48 $\mu$l) of 7.5 molar (M) ammonium acetate and 0.03 volumes of $MgCl_2$ and 2.5 volumes of ethanol, mixing, incubating at 4° C. for 12 hours, and centrifuging for 15 minutes at room temperature at 14,000 rpm. The DNA pellet is washed once with 500 $\mu$l of 70% ethanol, then air-dried and resuspended in 100 $\mu$l TE (10 mM Tris pH 8.0 and 1 mM EDTA) to give the purified full length promoter, in an isolated form.

EXAMPLE 8

Preparation of full-length promoter. A full-length promoter, in an isolated form, is obtained [SEQ ID NO: 20] by annealing together eight synthetic polynucleotides [SEQ ID NO: 21–28] using essentially the same procedures as described in Example 7.

EXAMPLE 9

Figure 6:
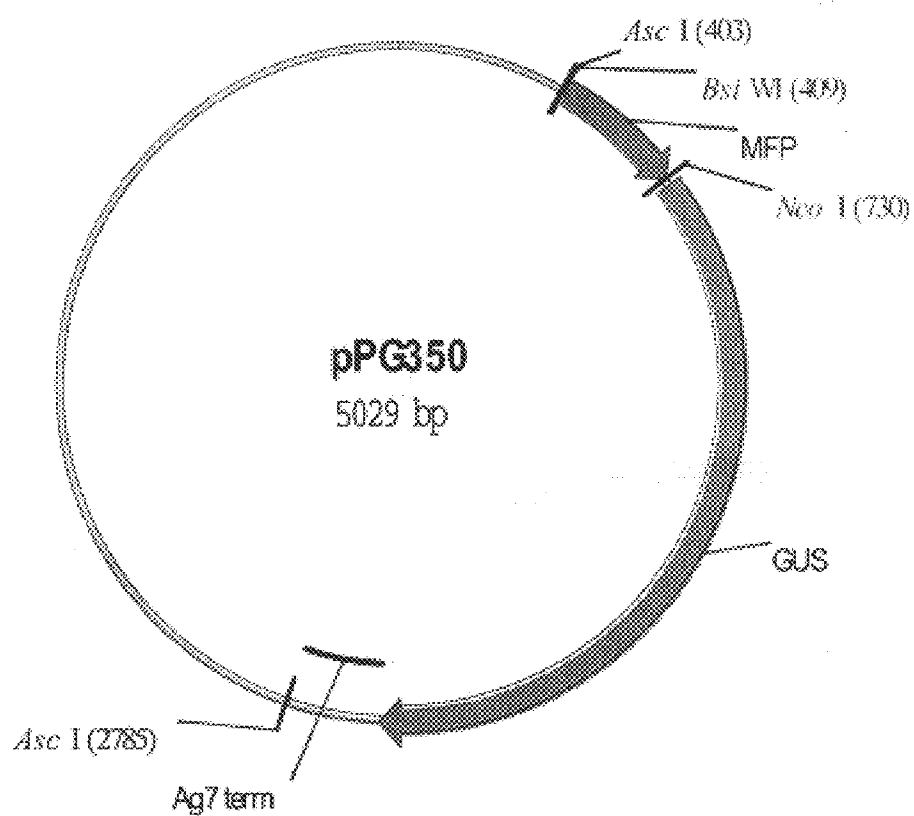
FIG. 6 is a diagram of plasmid pPG350.

Preparation of plasmid construct pPG350 containing the full length promoter from Example 7. Plasmid pPG350 is shown in FIG. 6. The plasmid construct pPG350 consists of 5029 basepairs. pPG350 is set forth as follows, wherein AscI, BsiWI, and NcoI, are restriction enzyme sites (numbers in parentheses indicate the nucleotide positions where the respective restriction enzyme cuts the DNA sequence). MFP is the modified full-length promoter, GUS (β-glucuronidase) is the structural gene as described hereinafter for pPG347, and Ag7 term is as described hereinafter for pPG344.

The preparation of plasmid construct pPG350 can be described as follows: Plasmid construct pPG347 is digested with the restriction enzymes BsiWI and NcoI, and the DNA fragment containing the vector backbone, the GUS coding region and the Ag7 terminator is isolated. In a ligation reaction, the modified full-length promoter (Seq. ID No. 11) with sticky BsiWI or NcoI sites at its 5'- or 3'-end, respectively, is ligated to this DNA fragment, yielding plasmid vector pPG350, containing the modified full-length promoter of Seq. ID No. 11.

EXAMPLE 10

Figure 7:
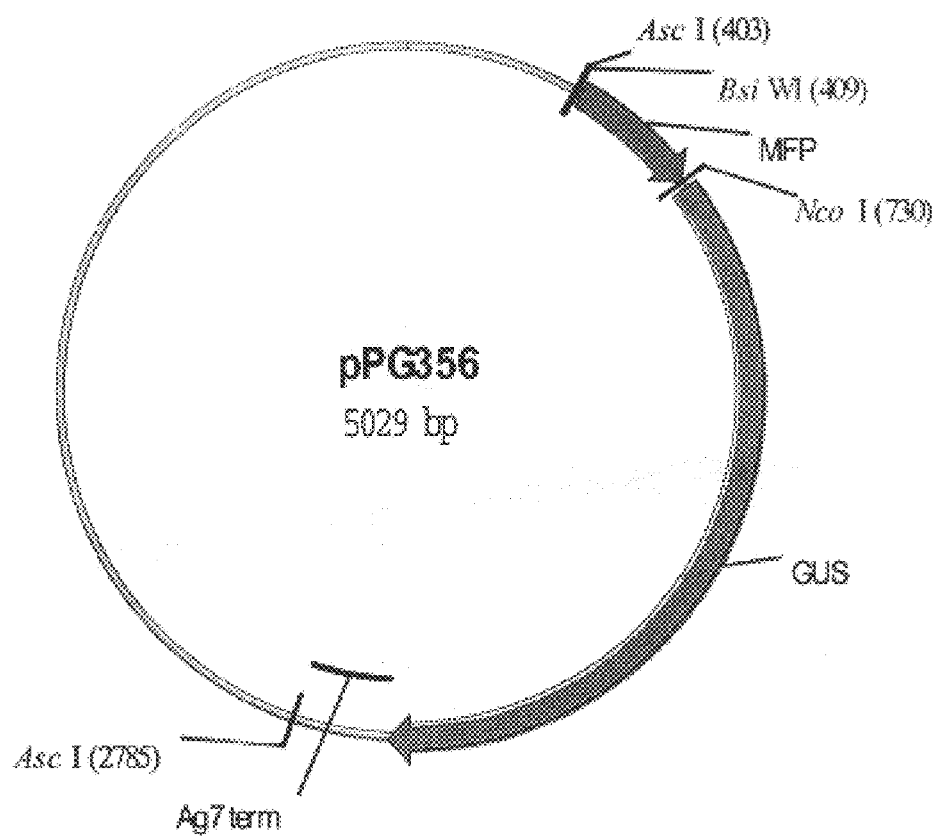
FIG. 7 is a diagram of plasmid pPG356.

Preparation of plasmid construct pPG356 containing the full length promoter from Example 8. Plasmid pPG356 is shown in FIG. 7. The plasmid construct pPG356 consists of 5029 basepairs. pPG356 is set forth as follows, wherein AscI, BsiWI, and NcoI, are restriction enzyme sites (numbers in parentheses indicate the nucleotide positions where the respective restriction enzyme cuts the DNA sequence). MFP is the modified full-length promoter, GUS (β-glucuronidase) is the structural gene as described hereinafter for pPG347, and Ag7 term is as described hereinafter for pPG344.

The preparation of plasmid construct pPG356 can be described as follows: Plasmid construct pPG347 is digested with the restriction enzymes BsiWI and NcoI, and the DNA fragment containing the vector backbone, the GUS coding region and the Ag7 terminator was isolated. In a ligation reaction, the modified full-length promoter (Seq. ID No. 20) with sticky BsiWI or NcoI sites at its 5'- or 3'-end, respectively, is ligated to this DNA fragment, yielding plasmid vector pPG356, containing the modified full-length promoter of Seq. ID No. 20.

EXAMPLE 10a

Figure 8:
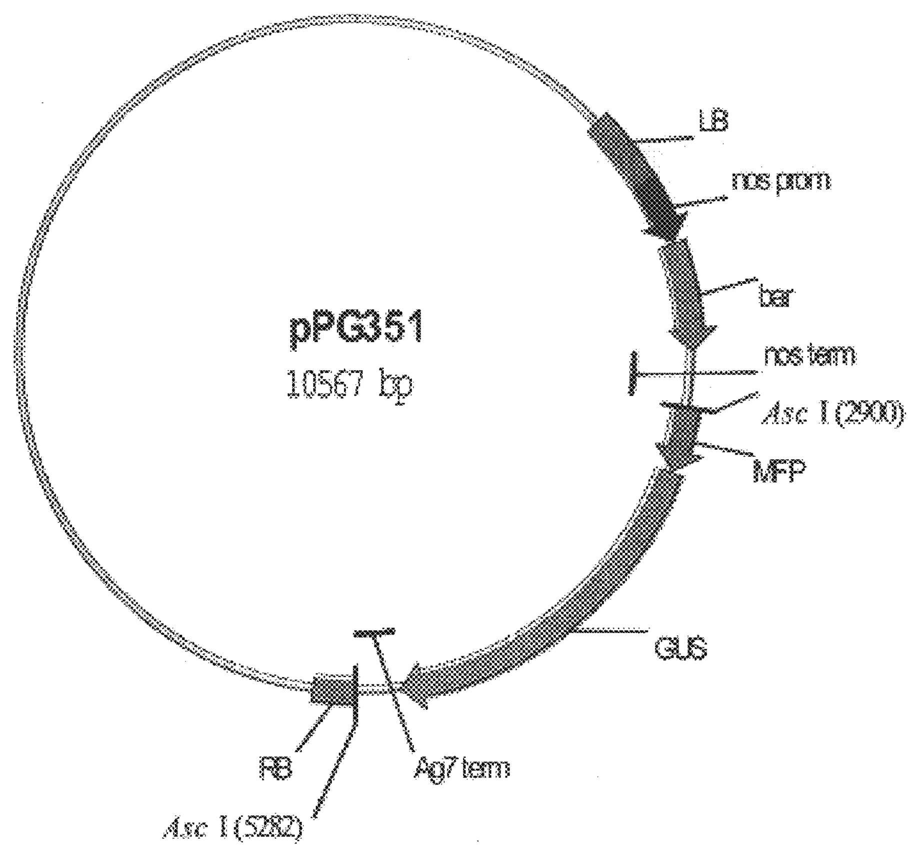
FIG. 8 is a diagram of plasmid pPG351.

Preparation of pPG351, a binary vector for Agrobacterium-mediated transformation that consists of 10567 basepairs. Plasmid pPG351is shown in FIG. 8. For construction of the binary vector pPG351, both plasmid construct pPG350 and binary vector pPG348 are digested with restriction enzyme AscI and the part of pPG350 containing the heterologous gene MFP (Seq. ID No, 11)-GUS-Ag7 is ligated into linearized binary vector pPG348, to yield binary vector pPG351, containing the heterologous gene MFP-GUS-Ag7. Restriction digests and ligation reactions are performed following common laboratory protocols that are known to those skilled in the art (such as Sambrook et al. 1989, *Molecular Cloning: A Laboratory Manual*). pPG351 is set forth as follows, wherein AscI is a restriction enzyme site (the number in parentheses indicates the nucleotide position where AscI cuts the DNA sequence). LB and RB are as described hereinafter for pPG348, nos prom, bar and nos term are as described hereinafter for pPG348, MFP, GUS and Ag7 term are as described hereinbefore for pPG350.

EXAMPLE 10b

Figure 9:
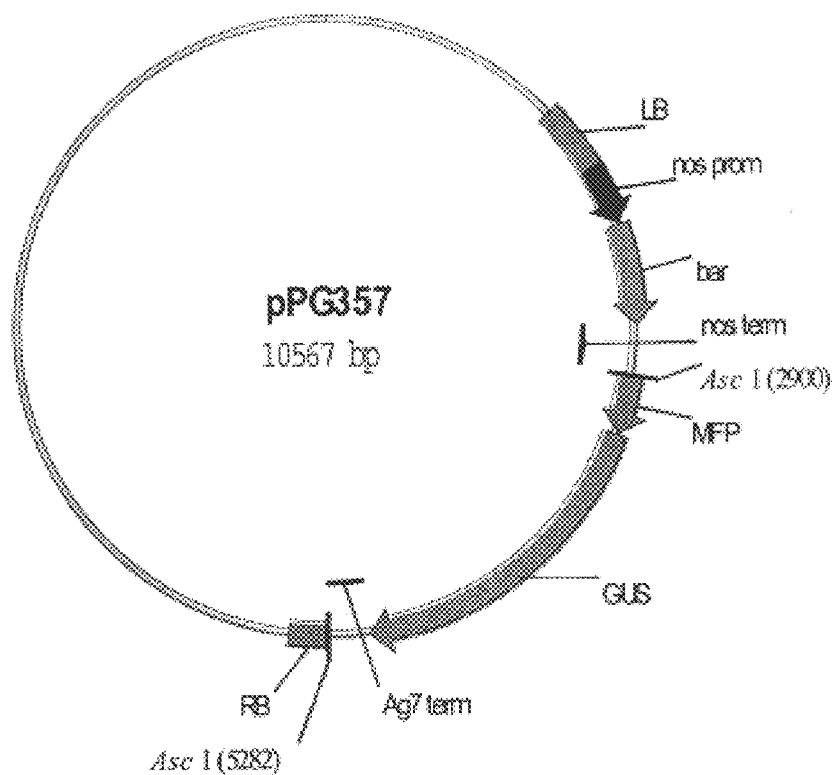
FIG. 9 is a diagram of plasmid pPG357.

Preparation of pPG357, a binary vector for Agrobacterium-mediated transformation that consists of 10567 basepairs. Plasmid pPG357 is shown in FIG. 9. For construction of the binary vector pPG357, both plasmid construct pPG356 and binary vector pPG348 are digested with restriction enzyme AscI and the part of pPG356 containing the heterologous gene MFP (Seq. ID No, 20)-GUS-Ag7 is ligated into linearized binary vector pPG348, to yield binary vector pPG357, containing the heterologous gene MFP-GUS-Ag7. Restriction digests and ligation reactions are performed following common laboratory protocols that are known to those skilled in the art (such as Sambrook et al. 1989, *Molecular Cloning: A Laboratory Manual*). pPG357 is set forth as follows, wherein AscI is a restriction enzyme site (the number in parentheses indicates the nucleotide position where AscI cuts the DNA sequence). LB and RB are as described hereinafter for pPG348, nos prom, bar and nos term are as described hereinafter for pPG348, MFP, GUS and Ag7 term are as described hereinbefore for pPG356.

EXAMPLE 11

Production of transgenic rice plants containing a modified full-length promoter and testing the function of the promoter in transgenic rice plants.

The procedure for transferring the plasmids to rice cells, producing transgenic plants and testing the function of the modified full-length promoter in the transgenic plants is essentially the same for plasmid construct pPG350 (containing the modified full-length promoter of Seq. ID No. 11) and pPG356 (containing the modified full-length promoter of Seq. ID No. 20).

Plasmid construct pPG350 or pPG356, containing the heterologous gene MFP-GUS-Ag7, is transferred to rice cells, transgenic rice cells are selected and from these transgenic rice cells, transgenic rice plants are regenerated. For selection of transgenic rice cells, plasmid construct pPG354, containing a hygromycin resistance gene which allows selection of transgenic cells with the antibiotic hygromycin B (as described in "Starting Materials"), is co-transformed to the rice cells. All plasmid vectors are transferred to rice suspension cells by particle bombardment. The activity of the GUS gene is subsequently tested in the primary regenerant plants and in the progeny plants of these primary regenerant plants. Only if the modified full-length promoter fulfills the function of a promoter, the GUS gene can be transcribed, eventually leading to blue stained cells upon incubation of tissue from transgenic plants in GUS staining solution.

The following is a description of production of transgenic rice plants containing the transgene from pPG350 or pPG356. (i.e. the heterologous gene MFP-GUS-Ag7), and analysis of the GUS expression in the primary regenerant plants and the progeny plants of these transgenic plants.

Rice suspension cells are bombarded as described in example 4, with pPG350 and pPG354 co-bombarded. After bombardment, the calli are cultured using a modified protocol as described by Burkhardt et al. in 1997 (Plant J 11: 1071–1078). Basically, one day after bombardment the bombarded calli are transferred to selective callus initiation medium containing 50 milligram per liter hygromycin B and are incubated for 4 weeks. Resistant calli growing on this medium are transferred to fresh selection medium for one week. Embryogenic calli are transferred to regeneration medium and regenerated plants are first transferred to rooting medium, later to soil. The presence of the GUS transgene in the transgenic plants is verified by Southern analysis using standard laboratory protocols as described in Potrykus and Spangenberg (Eds.) in 1995 (Gene Transfer to Plants. Springer-Verlag, Berlin Heidelberg, pp 221–228) using a radioactive labeled probe spanning the complete GUS gene. For detection of promoter activity, a small part of a young leaf from the regenerated plants is cut-off with a scalpel, and is immersed in GUS staining solution as described hereinbefore, and vacuum infiltrated for 5 minutes at 75 mmHg. GUS expression in the leaves which contain the heterologous transgene is detected by observing the incubated leaf pieces, or cross-sections thereof, under a stereomicroscope. Blue stained cells indicate expression of the GUS gene. To test the activity of the promoter also in progeny plants, the regenerated plants are grown to maturity and seeds are collected. For detection of promoter activity, the seeds are surface sterilized with 6% calcium hypochlorite for 10 minutes, rinsed with sterile distilled water and germinated on semi-solid agarose medium, containing half strength MS salts and vitamins (Sigma, M-5519), 20 grams per liter sucrose and 3.5 grams per liter agarose (pH 5.6). Five days after germination seedlings are immersed in GUS staining solution as described hereinbefore, and vacuum infiltrated for 5 minutes at 75 mmHg. GUS expression in the seedlings which contain the heterologous transgene is detected by observing the incubated seedlings, or cross-sections thereof, under a stereomicroscope.

Blue stained cells indicate expression of the GUS gene.

EXAMPLE 12

Production of transgenic *Arahidopsis thaliana* plants containing a modified full-length promoter and testing the function of the promoter in the transgenic *Arabidopsis thaliana* plants.

The procedure for Agrobacterium-mediated *Arabidopsis thaliana* transformation, screening for transgenic plants and testing the function of the modified full-length promoter in the transgenic plants is essentially the same for plasmid construct pPG351 (containing the modified full-length promoter of Seq. ID No. 11) and pPG357 (containing the modified full-length promoter of Seq. ID No. 20).

Binary vector pPG351 or pPG357, containing the heterologous gene MFP-GUS-Ag7, is transferred to a *Agrobacterium tumefaciens* strain (i.e. *Agrobacterium tumefaciens* strain LBA4404) and the T-DNA, containing the heterologous gene MFP-GUS-Ag7 from binary construct pPG351 or pPG357 is subsequently transferred by the Agrobacterium to cells from *Arabidopsis thaliana*. Transgenic *Arabidopsis thaliana* plants containing the heterologous gene MFP-GUS-Ag7 from binary construct pPG351 or pPG357 are selected and the activity of the GUS gene is subsequently tested in the selected plants and in the progeny plants of these plants.

The following is a description of production of transgenic *Arabidopsis thaliana* plants containing the transgene from pPG351 or pPG357 (i.e. the heterologous gene MFP-GUS-Ag7).

Transgenic *Arabidopsis thaliana* plants containing the T-DNA from binary vector pPG351 or pPG357 are produced using the floral dip method as described by Clough et al. in 1998 (Plant J 16: 735–743). Basically, plants are grown in soil until the primary inflorescence is about 10 cm tall. The primary inflorescence is cut to induce the emergence of multiple secondary inflorescences. The inflorescences of these plants are dipped in a suspension of *Agrobacterium tumefaciens*, strain LBA4404, containing the binary vector pPG351 or pPG357. After the dipping process, the plants are grown to maturity and the seeds are harvested. Transgenic seeds from these treated plants are selected by germination in soil and subsequent spraying with the chemical bialaphos (i.e. as contained in "Liberty", diluted 1:5000) on three consecutive days after the first true leaves of the plants have emerged. Transgenic plants containing the selectable "bar" marker gene (as described hereinafter in the description of pPG348 in "Starting Materials") survive this treatment and are transplanted to individual pots. The plants are grown to maturity and seeds are collected. For detection of the GUS gene activity in the selected plants, small leaf pieces are cut-off from the rosette leaves and are immersed in GUS staining solution and vacuum infiltrated for 5 minutes at 75 mmHg. GUS expression in the leaves which contain the heterologous gene is detected by observing the incubated leaves under a stereomicroscope. Blue stained cells indicate expression of the GUS gene and therefore functionality of the modified full-length promoter. For detection of the GUS gene activity in the progeny plants, the seeds derived from the selected plants are surface sterilized in chlorine gas as described by Ye et al. in 1999 (Plant J 19: 249–257) and germinated on semi-solid agarose medium, containing half strength MS salts and vitamins (Sigma, M-5519), 20 grams per liter sucrose and 3.5 grams per liter agarose (pH 5.6). Ten days after germination seedlings are immersed in GUS staining solution as described hereinbefore, and vacuum infiltrated for 5 minutes at 75 mmHg. GUS expression in the seedlings which contain the heterologous gene is detected by observing the incubated seedlings under a stereomicroscope. Blue stained cells indicate expression of the GUS gene and therefore functionality of the modified full-length promoter.

PREPARATION OF STARTING MATERIALS

Figure 10:
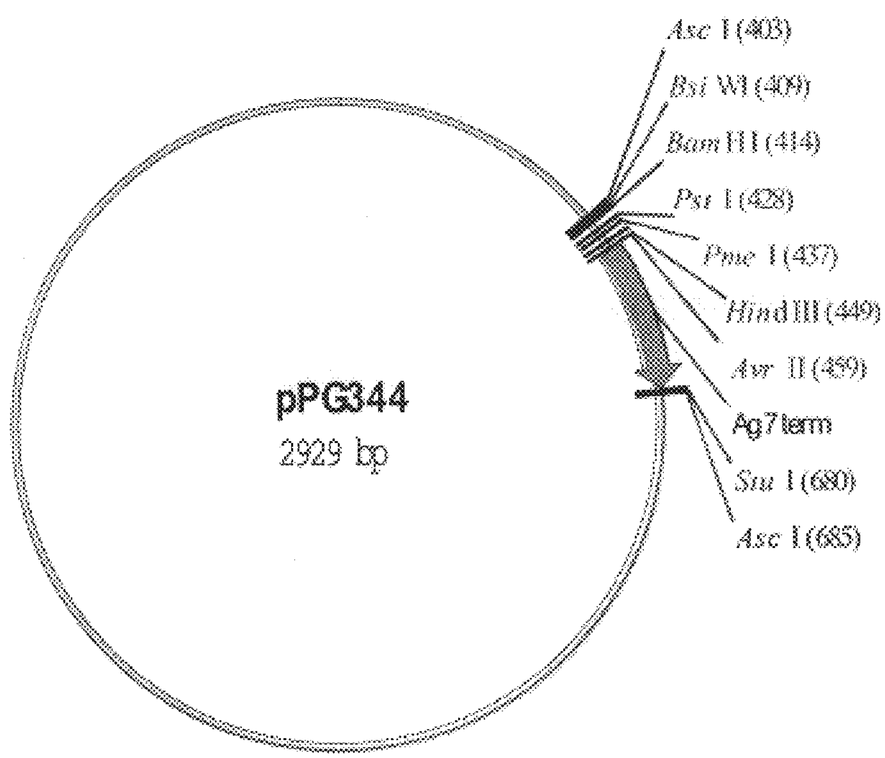
FIG. 10 is a diagram of plasmid pPG344.

The plasmid vector pPG344 consists of 2929 basepairs and is set forth as follows, wherein AscI, BsiWI, BamHI, PstI, PmeI, HindIII, AvrII, StuI, are restriction enzyme sites (numbers in parentheses indicate the nucleotide positions where the respective restriction enzyme cuts the DNA sequence). Plasmid pPG344 is shown in FIG. 10. This plasmid does not contain the minimal promoter. Ag7 term is as described hereinafter.

The plasmid pPG344 can be prepared from the plasmid pNEB193, available from New England Biolabs, Beverly, Mass., by removal of a HindIII-EcoRI fragment and replacement with an oligonucleotide containing all the shown restriction enzyme sites in the depicted order and insertion of a Ag7 terminator sequence into the AvrII and StuI restriction sites. All the necessary cloning steps for the replacement of the DNA sequence between (and including) the restriction sites HindIII and EcoRI from pNEB 193 with an oligonucleotide containing all the shown restriction sites is done following common laboratory protocols that are known to those skilled in the art (such as Sambrook et al. 1989*, Molecular Cloning: A Laboratory Manual*). The Ag7 terminator sequence is a sequence of 213 nucleotides from the 3' end of the gene number 7 from *Agrobacterium tumefaciens*. The sequence is derived from plasmid vector pGPTV-HPT as described by Becker et al. in 1992 (Plant Mol Biol 20:1195–1197). The sequence is amplified by a polymerase chain reaction (PCR) using forward primer 5'-TTCCCTAGGCCCGATGAGCTAAGCTAGCTATATC-3' and reverse primer 5'-GGGCGCGCCAGGCCTCCATCTTGAAAGAAATAT AGTTTAAATAT-3', the PCR product is digested with the restriction enzymes AvrII and StuI, and subsequently the AvrII/StuI fragment is ligated into the vector derived from pNEB193, containing the oligonucleotide with all the restriction sites, that was previously linearized with the restriction enzymes AvrII and StuI. All steps in this cloning procedure are performed following common laboratory protocols that are known to those skilled in the art (such as Sambrook et al. 1989*, Molecular Cloning: A Laboratory Manual*).

Figure 11:
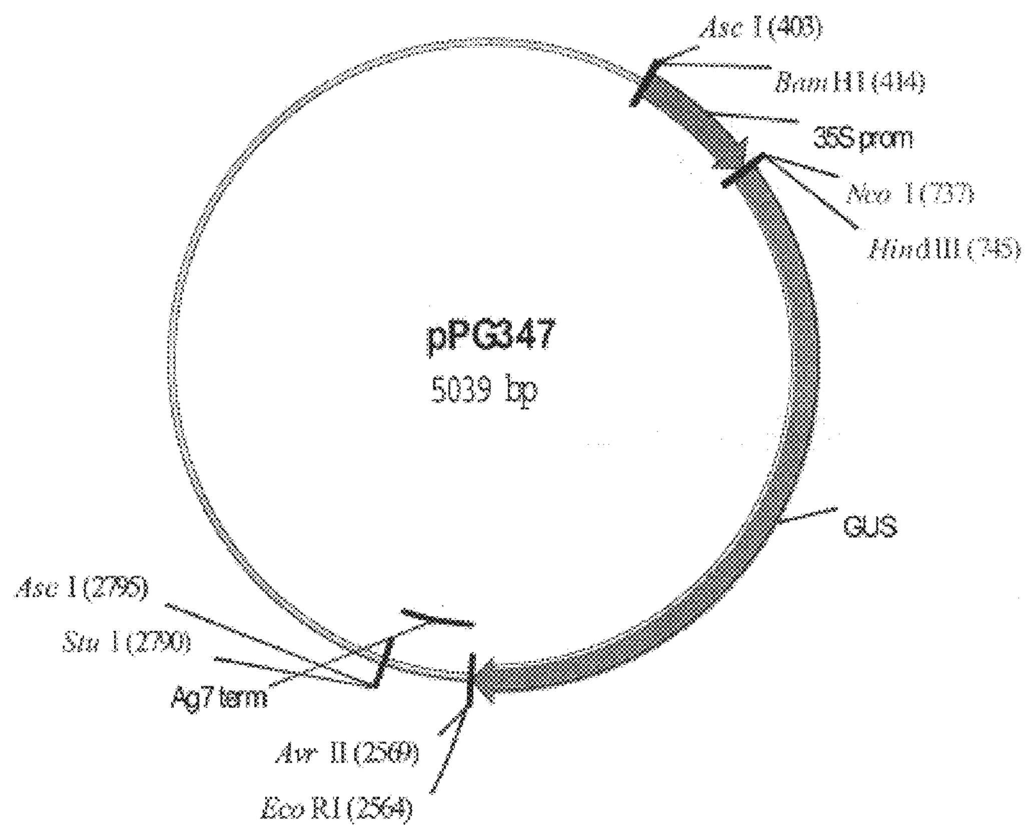
FIG. 11 is a diagram of plasmid pPG347.

The plasmid vector pPG347 consists of 5039 basepairs and is set forth as follows, wherein AscI, BamHI, NcoI, HindIII, EcoRI, AvrII, and StuI are restriction enzyme sites (numbers in parentheses indicate the nucleotide positions where the respective restriction enzyme cuts the DNA sequence). Plasmid pPG347 is shown in FIG. 11. Ag7 term is as described hereinbefore. 35S prom is a promoter sequence of 317 nucleotides from the genome of cauliflower mosaic virus. The sequence is derived from plasmid vector pGPTV-BLEO as described by Becker et al. in 1992 (Plant Mol Biol 20:1195–1197). The sequence is amplified by a polymerase chain reaction (PCR) using forward primer 5'-TTTGGATCCGAATTAATTCCCGATCCTATCTGTC ACTTC-3' and reverse primer 5'-AAACCATGGGTGATTTCAGCGTGTCCTCTCCAA ATG-3', the PCR product is digested with the restriction enzymes BamHI and NcoI, and subsequently the BamHI/NcoI fragment is ligated into pPG344, previously linearized with the restriction enzymes BamHI and NcoI. All steps in this cloning procedure are performed following common laboratory protocols that are known to those skilled in the art (such as Sambrook et al. 1989*, Molecular Cloning: A Laboratory Manual*).

Figure 12:
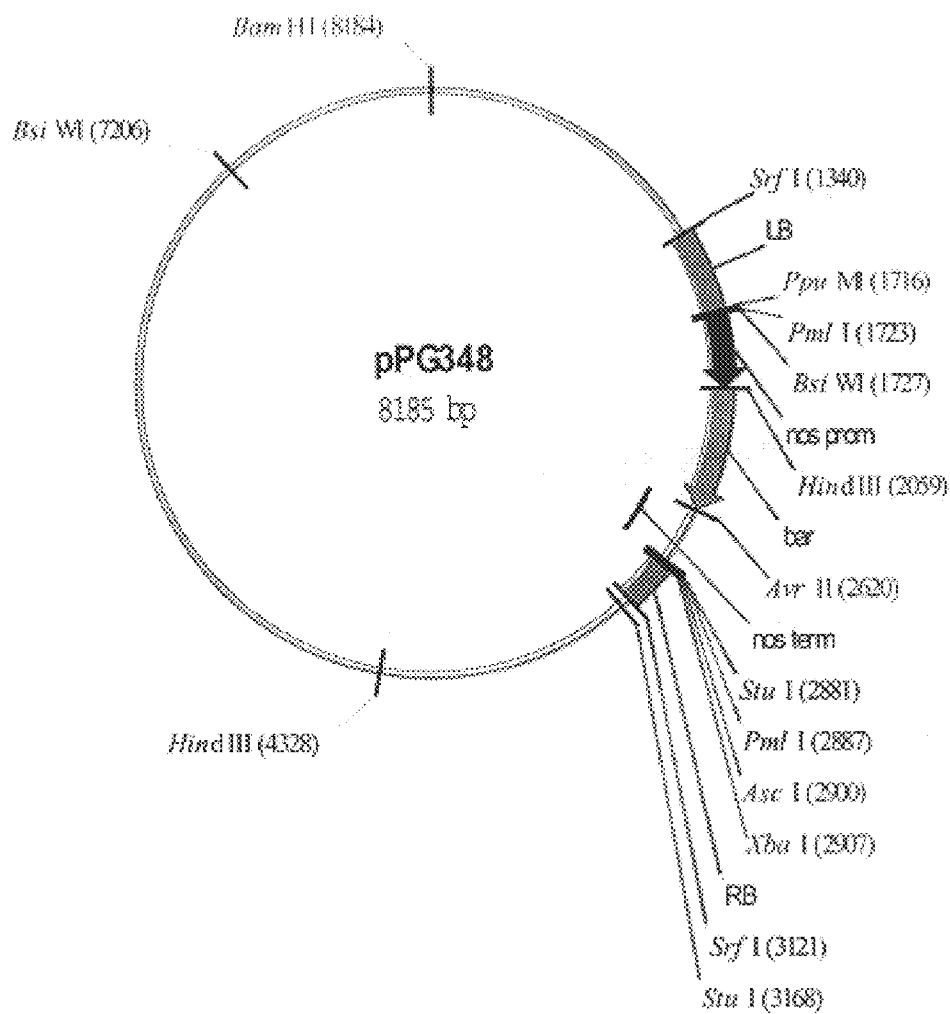
FIG. 12 is a diagram of plasmid pPG348.

The binary vector pPG348 consists of 8185 basepairs and is set forth as follows, wherein SrfI, PpuMI, PmlI, BsiWI, HindIII, AvrII, StuI, XbaI, and BamHI are restriction enzyme sites (numbers in parentheses indicate the nucleotide positions where the respective restriction enzyme cuts the DNA sequence). Plasmid pPG348 is shown in FIG. 12. LB and RB are left (LB; 380 basepairs) or right (RB; 205 basepairs) border sequences from the T-DNA region of *Agrobacterium tumefaciens* Ti plasmid pTi15955 (as described in NCBI accession number X00493). Nos prom is a promoter sequence of 327 basepairs and nos term a terminator sequence of 239 basepairs, both from the nopaline synthase gene of *Agrobacterium tumefaciens*. Bar is a structural gene, conferring resistance to the herbicidal compound bialaphos, from *Streptomyces hygroscopicus*. The binary vector pPG348 can be produced in the following way: A DNA sequence of 3850 basepairs (pVS), containing all necessary elements for replication and stabilization of the binary vector in *Agrobacterium tumefaciens* is derived from binary vector pCAMBIA1301 by a polymerase chain reaction (PCR) using forward primer 5'-TGGAAGCTTAACCACAGGGTTCCCCTCGGGA-3' and reverse primer 5'-TTTGGATCCAAGCTGTGACCGTCTCCGGGAG-3', creating a HindIII or a BamHI restriction site at the 5'-ends, respectively. A DNA sequence of 1339 basepairs (ColEI), containing all necessary elements for replication and stabilization of the binary vector in *Escherichia coli* is derived from binary vector pPZP111 by a polyrnerase chain reaction (PCR) using phosphorylated forward primer 5'-GGGCTCTACCAGGGCGCGGACAAG-3' and reverse primer 5'-TTTGGATCCCGCTTCGCCGGCGTTAACTC-3', creating a (cut) SrfI or a BamHI restriction site at the 5'-ends, respectively. A DNA sequence of 1202 basepairs (kanR), containing all necessary elements for production of aminoglycoside-3'-O-phosphotransferase in *E. coli* and *A. tumefaciens*, conferring resistance to kanamycin, is derived from binary vector pCAMBIA1301 by a polymerase chain reaction (PCR) using phosphorylated forward primer 5'-GGGCTGAGGTCTGCCTCGTGAAGAAG-3' and reverse primer 5'-GGAAAGCTTCGTTGTGTCTCAAAATCTCTG-3', creating a (cut) SrfI or a HindIII restriction site at the 5'-ends, respectively. LB and RB are derived from Ti plasmid pTi15955 by a polymerase chain reaction (PCR) using phosphorylated forward primer 5'-GGGCTGCGTCGGCTGATCTCACGGA-3' and reverse primer 5'-TTGGGGTCCTATTTATAATAACGCTGCGGA-3', creating a (cut) SrfI or a PpuMI restriction site at the 5'-ends (LB), or forward primer 5'-CCCTCTAGAGACTGGCAGGATATATAC-3' and phosphorylated reverse primer 5'-GGGCGGGTGTTCTGTCGTCTCGTTG-3', creating a XbaI or a (cut) SrfI restriction site at the 5'-ends (RB), respectively. LB and RB are digested with PpuMI or XbaI restriction enzymes, respectively, and ligated to a synthetic oligonucleotide, containing cut PpuMI or XbaI restriction sites, respectively, at its end and a PmlI and a AscI restriction site in between. The PCR products of pVS, ColEI and kanR are digested with the respective restriction enzymes and are used in a ligation reaction, containing the digested fragments of pVS, ColEI, kanR, and the ligated sequence containing the LB, the RB and the synthetic oligonucleotide. All these construction steps are performed following common laboratory protocols that are known to those skilled in the art (such as Sambrook et al. 1989*, Molecular Cloning: A Laboratory Manual*). Subsequently, a 1164 basepair PmlI-fragment containing a nos promoter, a coding sequence for a bar marker gene and a nos terminator is inserted into the PmlI restriction site by digesting the binary vector with PmlI restriction enzyme and ligating this linearized binary vector to the PmlI-fragment containing the bar gene. All these construction steps are performed following common laboratory protocols that are known to those skilled in the art (such as Sambrook et al. 1989*, Molecular Cloning: A Laboratory Manual*). The PmlI-fragment was derived as described in the following: The coding sequence for the bar gene is a sequence of 551 basepairs, derived from plasmid vector PGPTV-BAR as described by Becker et al. in 1992 (Plant Mol Biol 20:1195–1197). The sequence is amplified by a polymerase chain reaction (PCR) using forward primer 5'-CCCAAGCTTATGAGCCCAGAACGAC-3' and reverse primer 5'-ATTCCTAGGTCAGATCTCGGTGACG-3', the PCR product is digested with the restriction enzymes HindIII and AvrII, and subsequently the HindIII/AvrII fragment is ligated into plasmid vector pPG354, from which the aph4 gene has been removed with HindIII and AvrII. All steps in this cloning procedure are performed following common laboratory protocols that are known to those skilled in the art (such as Sambrook et al. 1989*, Molecular Cloning: A Laboratory Manual*).

Figure 13:
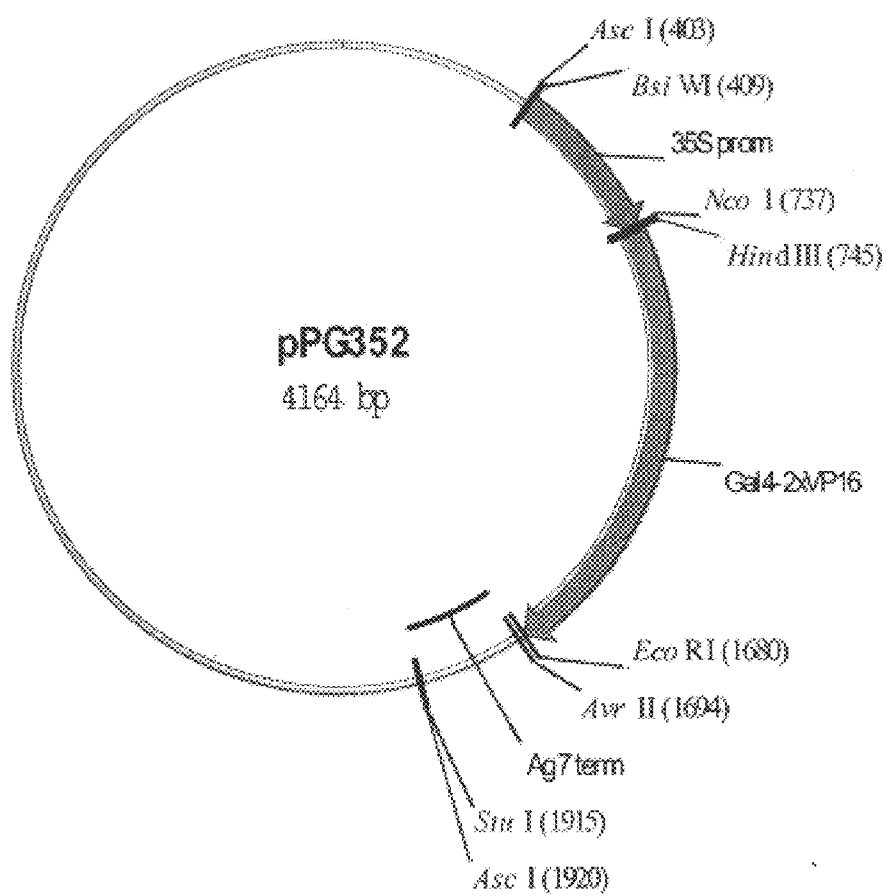
FIG. 13 is a diagram of plasmid pPG352.

The plasmid vector pPG352 consists of 4164 basepairs and is set forth as follows, wherein AscI, BsiWI, NcoI, HindIII, EcoRI, AvrII, and StuI are restriction enzyme sites (numbers in parentheses indicate the nucleotide positions where the respective restriction enzyme cuts the DNA sequence). Plasmid pPG352 is shown in FIG. 13. Ag7 term and 35S prom are as described hereinbefore. Gal4-2×VP16 is a coding sequence for a chimeric protein, containing a Gal4 DNA-binding domain and two copies of a VP16 activation domain, of 935 basepairs (HindIII/EcoRI-fragment) from vector Gal4/2×VP16, as described by Schwechheimer et al. in 1998 (Plant Mol Biol 36: 195–204). The HindIII/EcoRI-fragment is ligated into plasmid vector pPG347, after removing from pPG347 the GUS gene as a HindIII/EcoRI fragment. All steps in this cloning procedure are performed following common laboratory protocols that are known to those skilled in the art (such as Sambrook et al. 1989*, Molecular Cloning: A Laboratory Manual*).

Figure 14:
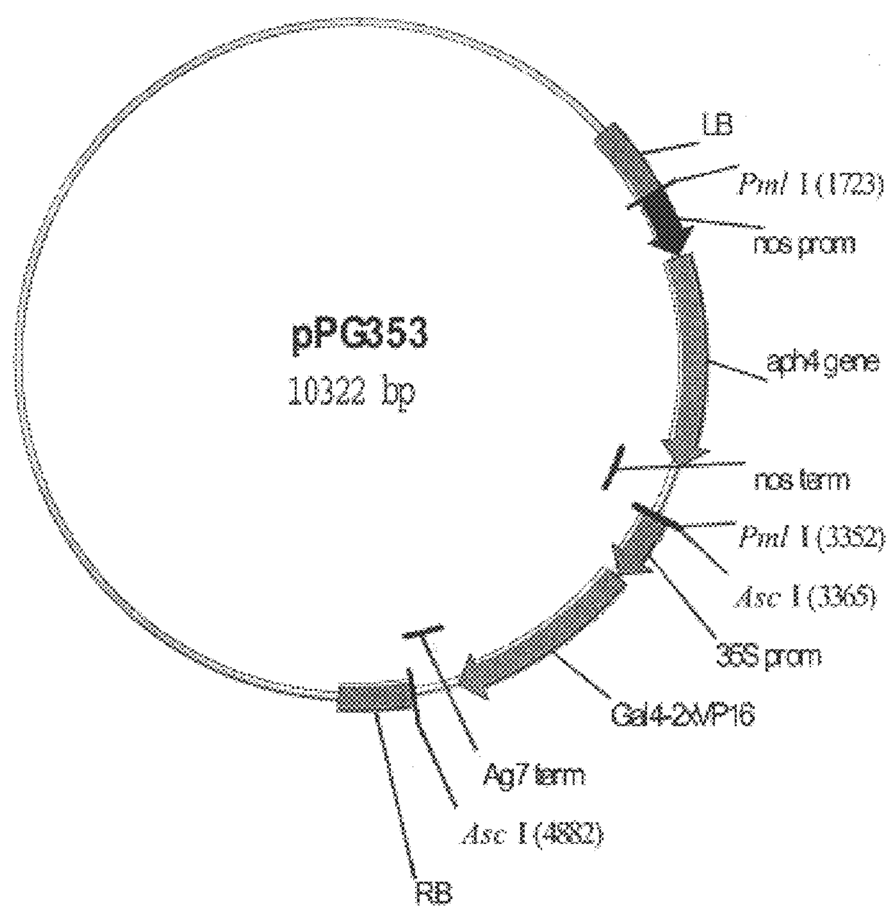
FIG. 14 is a diagram of plasmid pPG353.

The binary vector pPG353 consists of 10322 basepairs and is set forth as follows, wherein PmlI, and AscI are restriction enzyme sites (numbers in parentheses indicate the nucleotide positions where the respective restriction enzyme cuts the DNA sequence). Plasmid pPG353 is shown in FIG. 14. LB, RB, nos prom, nos term, 35S prom, Gal4-2×VP16, Ag7 term are as described hereinbefore, aph4 is as described hereinafter with plasmid construct pPG354. pPG353 can be constructed by replacing the PmlI-fragment in pPG348, containing the bar gene, with the PmlI-fragment from pPG354, containing the aph4 gene, and by subsequently cloning the AscI-fragment from pPG352, containing the chimeric Gal4-2×VP16 gene, into the AscI restriction site. All steps in this cloning procedure are performed following common laboratory protocols that are known to those skilled in the art (such as Sambrook et al. 1989*, Molecular Cloning: A Laboratory Manual*).

Figure 15:
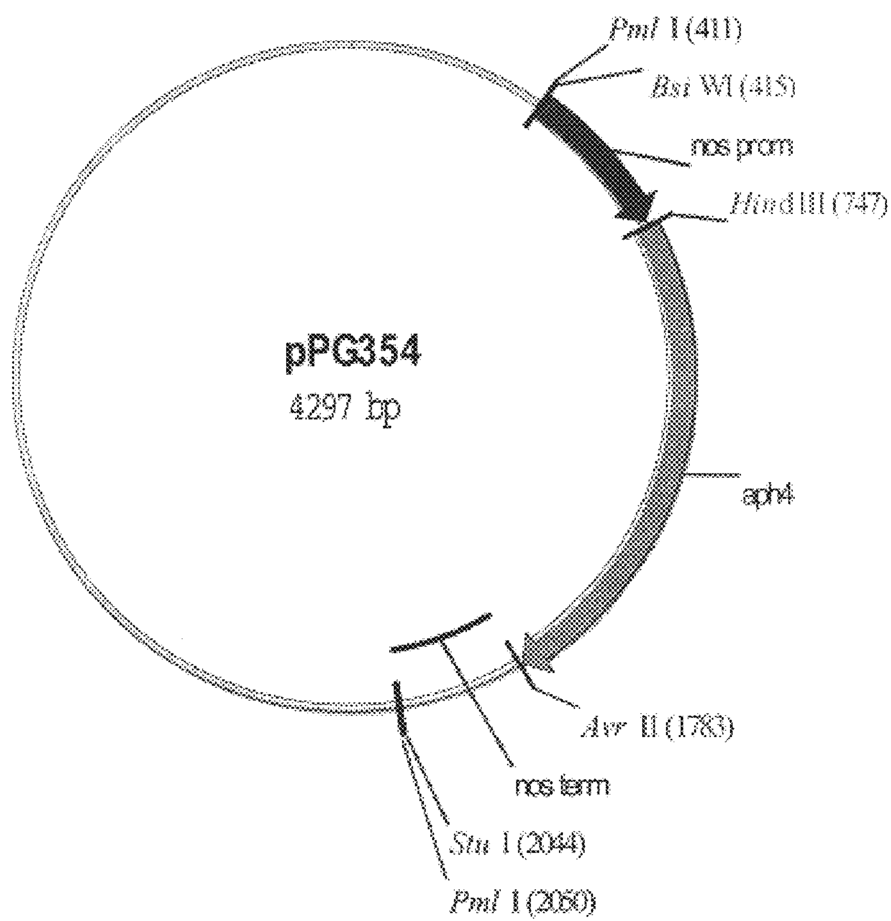
FIG. 15 is a diagram of plasmid pPG354.

The plasmid vector pPG354 consists of 4297 basepairs and is set forth as follows, wherein AscI, BsiWI, NcoI, HindIII, EcoRI, AvrII, and StuI are restriction enzyme sites (numbers in parentheses indicate the nucleotide positions where the respective restriction enzyme cuts the DNA sequence). Plasmid pPG354 is shown in FIG. 15. Nos prom and nos term are a promoter sequence of 318 or a terminator sequence of 253 basepairs, respectively, from the nopaline synthase from the Ti plasmid pTiC58 T-DNA region. Nos prom is derived from plasmid vector pGPTV-HPT as described by Becker et al. in 1992 (Plant Mol Biol 20:1195–1197). The sequence is amplified by a polymerase chain reaction (PCR) using phosphorylated forward primer 5'-CCACGTGCGTACGCTCGAGATCATGAGCGGAGA ATTAAG-3' and reverse primer 5'-GTGAAGCTTAGCCATGGCGAAACGATCGTCTAG-3', and the PCR product is digested with the restriction enzyme HindIII. Nos term is derived from plasmid vector pGPTV-HPT as described by Becker et al. in 1992 (Plant Mol Biol 20:1195–1197). The sequence is amplified by a polymerase chain reaction (PCR) using forward primer 5'-ATACCTAGGATCGTTCAAACATTTGG-3' and phosphorylated reverse primer 5'-CACGTGAGGCCTCGATCTAGTAACATAGATGAC-3', and the PCR product is digested with the restriction enzyme AvrII. Aph4 is the coding sequence for hygromycin phosphotransferase from *E. coli*, a sequence of 1026 basepairs derived from plasmid vector pGPTV-HPT as described by Becker et al. in 1992 (Plant Mol Biol 20:1195–1197). The sequence is amplified by a polymerase chain reaction (PCR) using forward primer 5'-CCGAAGCTTATGAAAAAGCCTGAACTCAC-3' and reverse primer 5'-TTCCCTAGGAATTCTATTCCTTTGCCCTCGGA-3', the PCR product is digested with the restriction enzymes HindIII and AvrII. Plasmid pNEB193, available from New England Biolabs, Beverly, Mass., is digested with HindIII and EcoRI and subsequently the overhanging DNA strands are filled-in in a Klenow enzyme reaction. Subsequently, this "blunted" vector is used in a ligation reaction together with the three fragments described above (nos prom, aph4, nos term), that have been digested with HindIII and/or AvrII. The resulting vector from this ligation reaction is pPG354.

What is claimed is:

1. DNA that is a) SEQ ID NO: 10;

b) the complementary sequence thereof; or c) the double stranded sequence of a) and b).

2. DNA of claim 1 that is SEQ ID NO: 11 or SEQ ID NO: 20.

3. A DNA construct comprising DNA that is a) SEQ ID NO: 10;

b) the complementary sequence thereof; or c) the double stranded sequence of a) and b).

4. The DNA construct of claim 3 that is SEQ ID NO: 11 or SEQ ID NO: 20.

5. The DNA construct of claim 3 that is a plasmid.

6. The DNA construct of claim 3 that is the plasmid pPG350 or pPG351 or pPG356 or pPG357.

7. A eukaryotic cell comprising DNA that is a) SEQ ID NO: 10;

b) the complementary sequence thereof; or c) the double stranded sequence of a) and b).

8. The eukaryotic cell of claim 7 comprising a DNA that is SEQ ID NO: 11 or SEQ ID NO: 20.

9. The eukaryotic cell of claim 7 wherein the cell is a plant cell.

10. The eukaryotic cell of claim 9 wherein the cell is a dicot plant cell.

11. The eukayrotic cell of claim 7 wherein the cell is a monocot plant cell.

12. A plant or plant part having a eukaryotic cell comprising DNA that is a) SEQ ID NO: 10;

b) the complementary sequence thereof; or c) the double stranded sequence of a) and b).

13. The plant or plant part of claim 12 having a eukaryotic cell comprising a DNA that is SEQ ID NO: 11 or SEQ ID NO: 20.

14. The plant or plant part of claim 12 that is, or is from, a dicot plant.

15. The plant or plant part of claim 12 that is, or is from, a monocot plant.

16. The plant or plant part of claim 12 that is, or is from, *Arabidopsis thaliana* or *Oryza sativa.*

17. Seed that can produce a plant containing DNA that is:

a) SEQ ID NO: 10;

b) the complementary sequence thereof; or c) the double stranded sequence of a) and b).

18. Seed of claim 17 wherein the DNA is SEQ ID NO: 11 or SEQ ID NO: 20.

19. Seed from a plant of claim 12.

20. A method of regulating the transcription of a heterologous gene in a plant or plant tissue comprising transforming the plant or plant tissue with a DNA construct comprising a heterologous gene and DNA that is:

a) SEQ ID NO: 10;

b) the complementary sequence thereof; or c) the double stranded sequence of a) and b).

* * * * *

SEQUENCE LISTING

```
<160> NUMBER OF SEQ ID NOS: 28

<210> SEQ ID NO 1
<211> LENGTH: 34
<212> TYPE: DNA
<213> ORGANISM: Artificial Sequence
<220> FEATURE:
<223> OTHER INFORMATION: Basepair sequence from  5' to 3' end for
      generic modified minimal promoter, not including cloning sites

<400> SEQUENCE: 1

tatataagga ggrsttcatt cccatttgaa ggat                              34


<210> SEQ ID NO 2
<211> LENGTH: 44
<212> TYPE: DNA
<213> ORGANISM: Artificial Sequence
<220> FEATURE:
<223> OTHER INFORMATION: Basepair sequence from  5' to 3' end for
      generic optimal modified minimal promoter, not including cloning
      sites
<220> FEATURE:
<223> OTHER INFORMATION: Description of Artificial Sequence: modified
      promoter

<400> SEQUENCE: 2

tcctctatat aaggaggrst tcattcccat ttgaaggatc aata                   44


<210> SEQ ID NO 3
<211> LENGTH: 49
<212> TYPE: DNA
<213> ORGANISM: Artificial Sequence
<220> FEATURE:
<223> OTHER INFORMATION: Basepair sequence from  5' to 3' end for
      generic optimal minimal promoter with additional nucleotides to be
      cloned into PstI and PmeI restriction sites

<400> SEQUENCE: 3

gtcctctata taaggaggrs ttcattccca tttgaaggat caatagttt              49


<210> SEQ ID NO 4
<211> LENGTH: 58
<212> TYPE: DNA
<213> ORGANISM: Artificial Sequence
<220> FEATURE:
<223> OTHER INFORMATION: Description of Artificial Sequence: basepair
      sequence for generic optimized minimal promoter, including
      complete PstI and PmeI cloning sites at the 5' and 3' -end,
      respectively

<400> SEQUENCE: 4

ctgcagtcct ctatataagg aggrsttcat tcccatttga aggatcaata gtttaaac    58


<210> SEQ ID NO 5
<211> LENGTH: 34
<212> TYPE: DNA
<213> ORGANISM: Artificial Sequence
<220> FEATURE:
<223> OTHER INFORMATION: Basepair sequence from  5' to 3' end for
      modified minimal promoter, not including nucleotides for cloning
<220> FEATURE:

<400> SEQUENCE: 5
```

-continued

```
tatataagga ggggttcatt cccatttgaa ggat                          34


<210> SEQ ID NO 6
<211> LENGTH: 44
<212> TYPE: DNA
<213> ORGANISM: Artificial Sequence
<220> FEATURE:
<223> OTHER INFORMATION: Basepair sequence from  5' to 3' end for
      optimal minimal promoter, not including nucleotides for cloning

<400> SEQUENCE: 6

tcctctatat aaggaggggt tcattcccat ttgaaggatc aata               44


<210> SEQ ID NO 7
<211> LENGTH: 49
<212> TYPE: DNA
<213> ORGANISM: Artificial Sequence
<220> FEATURE:
<223> OTHER INFORMATION: Basepair sequence from 5' to 3' end for
      optimized minimal promoter with additional nucleotides to be
      cloned into PstI and PmeI sites

<400> SEQUENCE: 7

gtcctctata taaggagggg ttcattccca tttgaaggat caatagttt          49


<210> SEQ ID NO 8
<211> LENGTH: 58
<212> TYPE: DNA
<213> ORGANISM: Artificial Sequence
<220> FEATURE:
<223> OTHER INFORMATION: Basepair sequence from  5' to 3' end for
      optimal minimal promoter, including complete PstI and PmeI cloning
      sites

<400> SEQUENCE: 8

ctgcagtcct ctatataagg aggggttcat tcccatttga aggatcaata gtttaaac    58


<210> SEQ ID NO 9
<211> LENGTH: 53
<212> TYPE: DNA
<213> ORGANISM: Artificial Sequence
<220> FEATURE:
<223> OTHER INFORMATION: Description of Artificial Sequence:
      complementary strand to sequence no 7 with additional nucleotides
      to be cloned into PstI and PmeI sites

<400> SEQUENCE: 9

aaactattga tccttcaaat gggaatgaac ccctccttat atagaggact gca     53


<210> SEQ ID NO 10
<211> LENGTH: 303
<212> TYPE: DNA
<213> ORGANISM: Artificial Sequence
<220> FEATURE:
<223> OTHER INFORMATION: Description of Artificial Sequence: Generic
      full length promoter

<400> SEQUENCE: 10

aatgaagtcc caatcctagt ggtcactttt gaaaggaacc ttggcaaagg agggtggctt     60

gcaagtgcca tccttgcrat aaaggaaagg tgaaggatca aggtgcccct accaamagtg    120

gtcttgcctt tggtccccca cccaagagga gcatcctagt acaagtgggg aatccaacca    180

cgtcttcgca agwggrttgw tgtgayatct ccattgaygt aagggatgac gcacaaagtg    240

actatccttc acaagacctt cctctatata aggaggggtt cattcccatt tgaaggatca    300
```

ata 303

<210> SEQ ID NO 11
<211> LENGTH: 303
<212> TYPE: DNA
<213> ORGANISM: Artificial Sequence
<220> FEATURE:
<223> OTHER INFORMATION: Description of Artificial Sequence: Specific full length sequence

<400> SEQUENCE: 11
aatgaagtcc caatcctagt ggtcactttt gaaaggaacc ttggcaaagg agggtggctt 60
gcaagtgcca tccttgcgat aaaggaaagg tgaaggatca aggtgcccct accaacagtg 120
gtcttgcctt tggtccccca cccaagagga gcatcctagt acaagtgggg aatccaacca 180
cgtcttcgca agagggttgt tgtgacatct ccattgatgt aagggatgac gcacaaagtg 240
actatccttc acaagacctt cctctatata aggaggggtt cattcccatt tgaaggatca 300
ata 303

<210> SEQ ID NO 12
<211> LENGTH: 94
<212> TYPE: DNA
<213> ORGANISM: Artificial Sequence
<220> FEATURE:
<223> OTHER INFORMATION: Description of Artificial Sequence: polynucleotides for making full length promoter, including additional nucleotides for a BamHI restriction site and to be cloned into a BsiWI site

<400> SEQUENCE: 12
gtacggatcc aatgaagtcc caatcctagt ggtcactttt gaaaggaacc ttggcaaagg 60
agggtggctt gcaagtgcca tccttgcgat aaag 94

<210> SEQ ID NO 13
<211> LENGTH: 80
<212> TYPE: DNA
<213> ORGANISM: Artificial Sequence
<220> FEATURE:
<223> OTHER INFORMATION: Description of Artificial Sequence: polynucleotides for making full length promoter

<400> SEQUENCE: 13
gaaaggtgaa ggatcaaggt gcccctacca acagtggtct tgcctttggt cccccaccca 60
agaggagcat cctagtacaa 80

<210> SEQ ID NO 14
<211> LENGTH: 80
<212> TYPE: DNA
<213> ORGANISM: Artificial Sequence
<220> FEATURE:
<223> OTHER INFORMATION: Description of Artificial Sequence: polynucleotides for making full length promoter

<400> SEQUENCE: 14
gtggggaatc caaccacgtc ttcgcaagag ggttgttgtg acatctccat tgatgtaagg 60
gatgacgcac aaagtgacta 80

<210> SEQ ID NO 15
<211> LENGTH: 67
<212> TYPE: DNA
<213> ORGANISM: Artificial Sequence
<220> FEATURE:
<223> OTHER INFORMATION: Description of Artificial Sequence:

-continued polynucleotides for making full length promoter, including additional nucleotides for a PmeI restriction site and to be cloned into a NcoI site

<400> SEQUENCE: 15
tccttcacaa gaccttcctc tatataagga ggggttcatt cccatttgaa ggatcaatag 60
tttaaac 67

<210> SEQ ID NO 16
<211> LENGTH: 70
<212> TYPE: DNA
<213> ORGANISM: Artificial Sequence
<220> FEATURE:
<223> OTHER INFORMATION: Description of Artificial Sequence: polynucleotides for making full length promoter, including additional nucleotides for a BamHI restriction site and to be cloned into a BsiWI site

<400> SEQUENCE: 16
ttgcaagcca ccctcctttg ccaaggttcc tttcaaaagt gaccactagg attgggactt 60
cattggatcc 70

<210> SEQ ID NO 17
<211> LENGTH: 80
<212> TYPE: DNA
<213> ORGANISM: Artificial Sequence
<220> FEATURE:
<223> OTHER INFORMATION: Description of Artificial Sequence: polynucleotides for making full length promoter

<400> SEQUENCE: 17
tgggtggggg accaaaggca agaccactgt tggtaggggc accttgatcc ttcacctttc 60
ctttatcgca aggatggcac 80

<210> SEQ ID NO 18
<211> LENGTH: 80
<212> TYPE: DNA
<213> ORGANISM: Artificial Sequence
<220> FEATURE:
<223> OTHER INFORMATION: Description of Artificial Sequence: polynucleotides for making full length promoter

<400> SEQUENCE: 18
ccttacatca atggagatgt cacaacaacc ctcttgcgaa gacgtggttg gattccccac 60
ttgtactagg atgctcctct 80

<210> SEQ ID NO 19
<211> LENGTH: 91
<212> TYPE: DNA
<213> ORGANISM: Artificial Sequence
<220> FEATURE:
<223> OTHER INFORMATION: Description of Artificial Sequence: polynucleotides for making full length promoter, including additional nucleotides for a PmeI restriction site and to be cloned into an Nco I restriction site

<400> SEQUENCE: 19
catggtttaa actattgatc cttcaaatgg gaatgaaccc ctccttatat agaggaaggt 60
cttgtgaagg atagtcactt tgtgcgtcat c 91

<210> SEQ ID NO 20
<211> LENGTH: 303
<212> TYPE: DNA
<213> ORGANISM: Artificial Sequence -continued
<220> FEATURE:
<223> OTHER INFORMATION: Description of Artificial Sequence: Specific full length sequence

<400> SEQUENCE: 20

```
aatgaagtcc caatcctagt ggtcactttt gaaaggaacc ttggcaaagg agggtggctt     60

gcaagtgcca tccttgcaat aaaggaaagg tgaaggatca aggtgcccct accaaaagtg    120

gtcttgcctt tggtccccca cccaagagga gcatcctagt acaagtgggg aatccaacca    180

cgtcttcgca agtggattga tgtgatatct ccattgacgt aagggatgac gcacaaagtg    240

actatccttc acaagacctt cctctatata aggaggggtt cattcccatt tgaaggatca    300

ata                                                                  303
```

<210> SEQ ID NO 21
<211> LENGTH: 94
<212> TYPE: DNA
<213> ORGANISM: Artificial Sequence
<220> FEATURE:
<223> OTHER INFORMATION: Description of Artificial Sequence: polynucleotides used to make the full length promoter, including additional nucleotides for BamHI restriction site and to be cloned into a BsiWI site

<400> SEQUENCE: 21

```
gtacggatcc aatgaagtcc caatcctagt ggtcactttt gaaaggaacc ttggcaaagg     60

agggtggctt gcaagtgcca tccttgcaat aaag                                 94
```

<210> SEQ ID NO 22
<211> LENGTH: 80
<212> TYPE: DNA
<213> ORGANISM: Artificial Sequence
<220> FEATURE:
<223> OTHER INFORMATION: Description of Artificial Sequence: polynucleotides used to make the full length promoter

<400> SEQUENCE: 22

```
gaaaggtgaa ggatcaaggt gcccctacca aaagtggtct tgcctttggt cccccaccca     60

agaggagcat cctagtacaa                                                 80
```

<210> SEQ ID NO 23
<211> LENGTH: 67
<212> TYPE: DNA
<213> ORGANISM: Artificial Sequence
<220> FEATURE:
<223> OTHER INFORMATION: Description of Artificial Sequence: polynucleotides used to make the full length promoter

<400> SEQUENCE: 23

```
tccttcacaa gaccttcctc tatataagga ggggttcatt cccatttgaa ggatcaatag     60

tttaaac                                                               67
```

<210> SEQ ID NO 24
<211> LENGTH: 67
<212> TYPE: DNA
<213> ORGANISM: Artificial Sequence
<220> FEATURE:
<223> OTHER INFORMATION: Description of Artificial Sequence: polynucleotides used to make the full length promoter, including additional nucleotides for a PmeI restriction site and to be cloned into an Nco I restriction site

<400> SEQUENCE: 24

```
tccttcacaa gaccttcctc tatataagga ggggttcatt cccatttgaa ggatcaatag     60
```

-continued

```
tttaaac                                                             67


<210> SEQ ID NO 25
<211> LENGTH: 70
<212> TYPE: DNA
<213> ORGANISM: Artificial Sequence
<220> FEATURE:
<223> OTHER INFORMATION: Description of Artificial Sequence:
      polynucleotides used to make the full length promoter, including
      additional nucleotides a Bam HI restriction site and to be cloned
      into a BsiWI site

<400> SEQUENCE: 25

ttgcaagcca ccctcctttg ccaaggttcc tttcaaaagt gaccactagg attgggactt     60

cattggatcc                                                            70


<210> SEQ ID NO 26
<211> LENGTH: 80
<212> TYPE: DNA
<213> ORGANISM: Artificial Sequence
<220> FEATURE:
<223> OTHER INFORMATION: Description of Artificial Sequence:
      polynucleotides used to make the full length promoter

<400> SEQUENCE: 26

tgggtggggg accaaaggca agaccacttt tggtaggggc accttgatcc ttcacctttc     60

ctttattgca aggatggcac                                                 80


<210> SEQ ID NO 27
<211> LENGTH: 80
<212> TYPE: DNA
<213> ORGANISM: Artificial Sequence
<220> FEATURE:
<223> OTHER INFORMATION: Description of Artificial Sequence:
      polynucleotides used to make the full length promoter

<400> SEQUENCE: 27

ccttacgtca atggagatat cacatcaatc cacttgcgaa gacgtggttg gattccccac     60

ttgtactagg atgctcctct                                                 80


<210> SEQ ID NO 28
<211> LENGTH: 91
<212> TYPE: DNA
<213> ORGANISM: Artificial Sequence
<220> FEATURE:
<223> OTHER INFORMATION: Description of Artificial Sequence:
      polynucleotides used to make the full length promoter, including
      additional nucleotides for a PmeI restriction site and to be
      cloned into an Nco I site

<400> SEQUENCE: 28

catggtttaa actattgatc cttcaaatgg gaatgaaccc ctccttatat agaggaaggt     60

cttgtgaagg atagtcactt tgtgcgtcat c                                    91
```